(12) United States Patent
Irisawa et al.

(10) Patent No.: US 11,375,983 B2
(45) Date of Patent: Jul. 5, 2022

(54) ACOUSTIC WAVE IMAGE DISPLAY DEVICE AND METHOD

(71) Applicant: FUJIFILM Corporation, Tokyo (JP)

(72) Inventors: Kaku Irisawa, Kanagawa (JP); Dai Murakoshi, Kanagawa (JP); Tomoki Inoue, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 933 days.

(21) Appl. No.: 16/104,473

(22) Filed: Aug. 17, 2018

(65) Prior Publication Data

US 2019/0008484 A1 Jan. 10, 2019

Related U.S. Application Data

(63) Continuation of application No. PCT/JP2017/006156, filed on Feb. 20, 2017.

(30) Foreign Application Priority Data

Feb. 22, 2016 (JP) .............................. JP2016-030754

(51) Int. Cl.
*A61B 8/08* (2006.01)
*A61B 8/00* (2006.01)
(Continued)

(52) U.S. Cl.
CPC .......... *A61B 8/5261* (2013.01); *A61B 5/0095* (2013.01); *A61B 5/02007* (2013.01);
(Continued)

(58) Field of Classification Search
CPC ......... A61B 8/5261; A61B 8/14; A61B 8/463; A61B 8/465; A61B 8/467; A61B 8/5246;
(Continued)

(56) References Cited

U.S. PATENT DOCUMENTS

| | | | |
|---|---|---|---|
| 2013/0199300 A1 | 8/2013 | Abe | |
| 2013/0338475 A1* | 12/2013 | Herzog | A61B 5/0095 600/407 |

(Continued)

FOREIGN PATENT DOCUMENTS

| | | |
|---|---|---|
| JP | 2013-158531 A | 8/2013 |
| JP | 2015-523137 A | 8/2015 |
| JP | 2015-181660 A | 10/2015 |

OTHER PUBLICATIONS

International Preliminary Report on Patentability and Written Opinion of the International Searching Authority (forms PCT/IB/373, PCT/ISA/237 and PCT/IB/326), dated Sep. 7, 2018, for corresponding International Application No. PCT/JP2017/006156, with an English translation of the WO.

(Continued)

*Primary Examiner* — Amelie R Davis
*Assistant Examiner* — Marjan Saboktakin
(74) *Attorney, Agent, or Firm* — Birch, Stewart, Kolasch & Birch, LLP

(57) ABSTRACT

A first acoustic wave image and a second acoustic wave image are displayed on top of each other in different display colors, and a first operation icon for selecting the first acoustic wave image and a second operation icon for selecting the second acoustic wave image are displayed on operation icon display unit. The first operation icon and the second operation icon are displayed on top of each other in a display order identical to a display order of the first acoustic wave image and the second acoustic wave image that are displayed on top of each other on image display unit.

18 Claims, 12 Drawing Sheets

(51) Int. Cl.
 *A61B 5/00* (2006.01)
 *A61B 5/02* (2006.01)
 *A61B 8/14* (2006.01)
 *G01S 7/52* (2006.01)

(52) U.S. Cl.
 CPC ............ *A61B 5/6852* (2013.01); *A61B 5/742* (2013.01); *A61B 8/14* (2013.01); *A61B 8/463* (2013.01); *A61B 8/465* (2013.01); *A61B 8/467* (2013.01); *A61B 8/5246* (2013.01); *G01S 7/52071* (2013.01); *G01S 7/52074* (2013.01); *A61B 5/7257* (2013.01); *A61B 2562/0204* (2013.01)

(58) Field of Classification Search
 CPC . A61B 5/0095; A61B 5/02007; A61B 5/6852; A61B 5/742; G01S 7/52071; G01S 7/52074
 USPC .......................................................... 600/400
 See application file for complete search history.

(56) References Cited

U.S. PATENT DOCUMENTS

| | | | |
|---|---|---|---|
| 2014/0180087 A1* | 6/2014 | Millett | A61B 8/4416 600/437 |
| 2015/0062288 A1* | 3/2015 | Lee | H04N 5/44504 348/36 |
| 2015/0265156 A1* | 9/2015 | Tanaka | A61B 5/0095 600/473 |
| 2018/0028157 A1* | 2/2018 | Li | A61B 8/0891 |

OTHER PUBLICATIONS

International Search Report (form PCT/ISA/210), dated Jun. 27, 2017, for corresponding International Application No. PCT/JP2017/006156, with an English translation.
Japanese Office Action for Japanese Application No. 2018-501670, dated Feb. 5, 2019, with English translation.

* cited by examiner

ACOUSTIC WAVE IMAGE DISPLAY DEVICE AND METHOD

CROSS-REFERENCE TO RELATED APPLICATIONS

This application is a continuation application of International Application No. PCT/JP2017/006156, filed Feb. 20, 2017, the disclosure of which is incorporated herein by reference in its entirety. Further, this application claims priority from Japanese Patent Application No. 2016-030754, filed Feb. 22, 2016, the disclosure of which is incorporated herein by reference in its entirety.

BACKGROUND

1. Technical Field

The present invention relates to a method for displaying an acoustic wave image and a device that performs the method.

2. Related Art

Noninvasive measurement (photoacoustic measurement) that uses the photoacoustic effect has attracted attention in recent years. In photoacoustic measurement, for example, pulsed light of the wavelength range of visible light, near-infrared light, or intermediate infrared light is emitted to a subject. A light-absorbing material in the subject absorbs energy of the pulsed light and generates elastic waves (photoacoustic waves). In photoacoustic measurement, the photoacoustic waves are detected to quantitatively measure the concentration and the like of the light-absorbing material. Examples of the light-absorbing material in the subject include glucose and hemoglobin contained in blood. Further, an image (photoacoustic image) is generated on the basis of the detected photoacoustic waves to produce an image of distribution in the light-absorbing material within the subject. Such a technology for generating a photoacoustic image is called photoacoustic imaging (PAI) or photo acoustic tomography (PAT).

For example, JP2013-158531A and JP2015-181660A disclose devices for acquiring a photoacoustic image through photoacoustic imaging. JP2015-181660A describes a photoacoustic image acquisition device that is configured to acquire not only a photoacoustic image but also a so-called reflected ultrasound image.

Typically, a device for acquiring a reflected ultrasound image acquires a tomographic image or the like of the inside of the subject on the basis of signals obtained by detecting reflected acoustic waves, which are acoustic waves (mostly ultrasonic waves) transmitted to the subject and reflected within the subject. In contrast, a photoacoustic image acquisition device typically emits light such as laser light to the subject and acquires a photoacoustic image indicating distribution in the light-absorbing material within the subject on the basis of signals obtained by detecting photoacoustic waves generated from within the subject which has absorbed the light. In this specification, images acquired by these two types of devices are collectively referred to as acoustic wave images.

For example, a so-called ultrasound B-mode image, which is an example of the former acoustic wave image and one type of reflected ultrasound image, favorably shows, for example, a tomographic cross section of the inside of the subject. In contrast, a photoacoustic image favorably shows a light-absorbing body such as blood vessels in the subject. In the display of the images, the reflected ultrasound image and the photoacoustic image are commonly displayed superimposed on each other. An image represented by superimposing two types of acoustic wave images on each other is value in use in the clinical and medical research field.

SUMMARY

Now, consideration is given to a device capable of acquiring both a reflected ultrasound image and a photoacoustic image, in which when two types of acoustic wave images are displayed superimposed on each other on an image display device, a unique process is performed on one of the acoustic wave images or a process for hiding one of the acoustic wave images is performed.

In the device described above, if wide-ranging processes are to be performed on the acoustic wave images, it is presumable that a so-called GUI (graphical user interface) is used to perform an input operation to select an image to be processed or to designate a process.

However, conventional devices configured to perform an input operation by using a GUI have room for improvement in terms of accurate identification of each of a plurality of acoustic wave images displayed superimposed on each other on an image display screen.

The present invention has been made in view of the foregoing problem, and it is an object of the present invention to provide a device for displaying a plurality of acoustic wave images including a photoacoustic image, in which each of the plurality of acoustic wave images can be accurately identified.

An acoustic wave image display device according to the present invention is an acoustic wave image display device in a system for displaying a first acoustic wave image and a second acoustic wave image on image display unit, the first acoustic wave image being generated on the basis of detected signals of photoacoustic waves generated, from within a subject, by receiving light emitted to the subject, the second acoustic wave image being generated on the basis of detected signals of reflected acoustic waves, which are acoustic waves transmitted to the subject and reflected within the subject, the acoustic wave image display device including:

an image display control unit that causes the first acoustic wave image and the second acoustic wave image to be displayed on top of each other on the image display unit in different display colors;

operation icon display unit for displaying a first operation icon for selecting the first acoustic wave image and a second operation icon for selecting the second acoustic wave image; and an operation icon display control unit that causes the first operation icon and the second operation icon to be displayed on top of each other on the operation icon display unit in a display order identical to a display order of the first acoustic wave image and the second acoustic wave image that are displayed on top of each other on the image display unit.

Desirably, the acoustic wave image display device according to the present invention further includes: menu icon display unit for displaying a first menu icon group for designating a process to be performed on the first acoustic wave image and a second menu icon group for designating a process to be performed on the second acoustic wave image; and a menu icon display control unit that causes the first menu icon group and the second menu icon group to be displayed on the menu icon display unit in separate groups.

In the acoustic wave image display device according to the present invention, desirably, the menu icon display unit has a different display screen from the image display unit.

Alternatively, the menu icon display unit may have a display screen common to the image display unit.

In the acoustic wave image display device according to the present invention, desirably, the image display control unit changes the display order of the first acoustic wave image and the second acoustic wave image on the image display unit in accordance with an operation of changing an order in which the first operation icon and the second operation icon are stacked on top of each other.

In the configuration described above, desirably, the image display control unit causes the first acoustic wave image and the second acoustic wave image to be displayed in display colors determined in advance in accordance with a display order on the image display unit.

When the display colors are displayed in the way described above, desirably, the image display control unit causes an acoustic wave image located on a close side (acoustic wave image closer to an observer of the first acoustic wave image and the second acoustic wave image) in the display order to be displayed in a display color that makes a display color of an acoustic wave image located on a far side (acoustic wave image farther from the observer (acoustic wave image located behind the acoustic wave image) in the display order visible.

Further, in the acoustic wave image display device according to the present invention, desirably, each time a predetermined operation is applied to the first operation icon once, the image display control unit switches a display state (switches a display state of the first acoustic wave image) between a state in which the first acoustic wave image is displayed on the image display unit and a state in which the first acoustic wave image is hidden on the image display unit, and each time a predetermined operation is applied to the second operation icon once, the image display control unit switches a display state (switches a display state of the second acoustic wave image) between a state in which the second acoustic wave image is displayed on the image display unit and a state in which the second acoustic wave image is hidden on the image display unit.

The "predetermined operation" described above does not refer to a certain specific operation but refers to a certain operation determined in advance. Examples of the operation include a press-and-hold and a tap when the icon display screen is a touch panel, and a double-click when the icon display screen is a screen that also shows a cursor using a pointer such as a mouse.

In the configuration described above, desirably, the operation icon display control unit causes the operation icon for selecting, from among the first acoustic wave image and the second acoustic wave image, an acoustic wave image brought into the state in which the acoustic wave image is displayed to be displayed in a first form, and causes the operation icon for selecting, from among the first acoustic wave image and the second acoustic wave image, an acoustic wave image brought into the state in which the acoustic wave image is hidden to be displayed in a second form different from the first form.

Desirably, the first form is a form in which the operation icon is displayed in color, and the second form is a form in which the operation icon is represented by a contour.

Alternatively, the first form may be a form in which the operation icon is displayed in color, and the second form may be a form in which the operation icon is displayed in an achromatic color.

Alternatively, the first form may be a form in which a colored portion contains a character in a color different from a color of the colored portion to show an operation icon, and the second form may be a form in which the color of the colored portion and the color of the character in the first form are inverted.

Alternatively, the first form may be a form in which the operation icon is displayed in color, and the second form may be a form in which a predetermined sign is applied to the operation icon.

Further, in the acoustic wave image display device according to the present invention, desirably, the operation icon display control unit causes, among the first operation icon and the second operation icon, an operation icon located on a close side of the operation icon display unit (operation icon located on a side of the operation icon display means closer to an observer of the first operation icon and the second operation icon) in the display order to be displayed in a transparent manner to make an operation icon located on a far side of the operation icon display unit (operation icon located on a side of the operation icon display means farther from the observer (operation icon located behind the operation icon)) in the display order visible, and the image display control unit causes, among the first acoustic wave image and the second acoustic wave image, an acoustic wave image located on the close side in the display order to be displayed in a transparent manner to make an acoustic wave image located on the far side in the display order visible.

The "transparent manner" described above refers to both a fully transparent manner and a semi-transparent manner.

In the configuration described above, desirably, at least one of the operation icon display control unit or the image display control unit is capable of adjusting a degree of transparency in the display in a transparent manner.

Further, in the acoustic wave image display device according to the present invention, desirably, the operation icon display unit has a different display screen from the image display unit.

Alternatively, the operation icon display unit may have a display screen common to the image display unit.

An acoustic wave image display method according to the present invention is an acoustic wave image display method for displaying a first acoustic wave image and a second acoustic wave image in color on image display unit, the first acoustic wave image being generated on the basis of detected signals of photoacoustic waves generated, from within a subject, by the subject receiving light emitted to the subject, the second acoustic wave image being generated on the basis of detected signals of reflected acoustic waves, which are acoustic waves transmitted to the subject and reflected within the subject, the acoustic wave image display method including:

displaying the first acoustic wave image and the second acoustic wave image on top of each other in different display colors;

displaying, on operation icon display unit, a first operation icon for selecting the first acoustic wave image and a second operation icon for selecting the second acoustic wave image; and displaying the first operation icon and the second operation icon on top of each other in a display order identical to a display order of the first acoustic wave image and the second acoustic wave image that are displayed on top of each other on the image display unit.

According to an acoustic wave image display device and method of the present invention, it is possible to intuitively and accurately identify each of a plurality of acoustic wave images.

BRIEF DESCRIPTION OF THE DRAWINGS

Exemplary embodiments according to the technique of the present disclosure will be described in detail based on the following figures, wherein.

DESCRIPTION

The following describes an embodiment of the present invention in detail with reference to the drawings.

Figure 1:
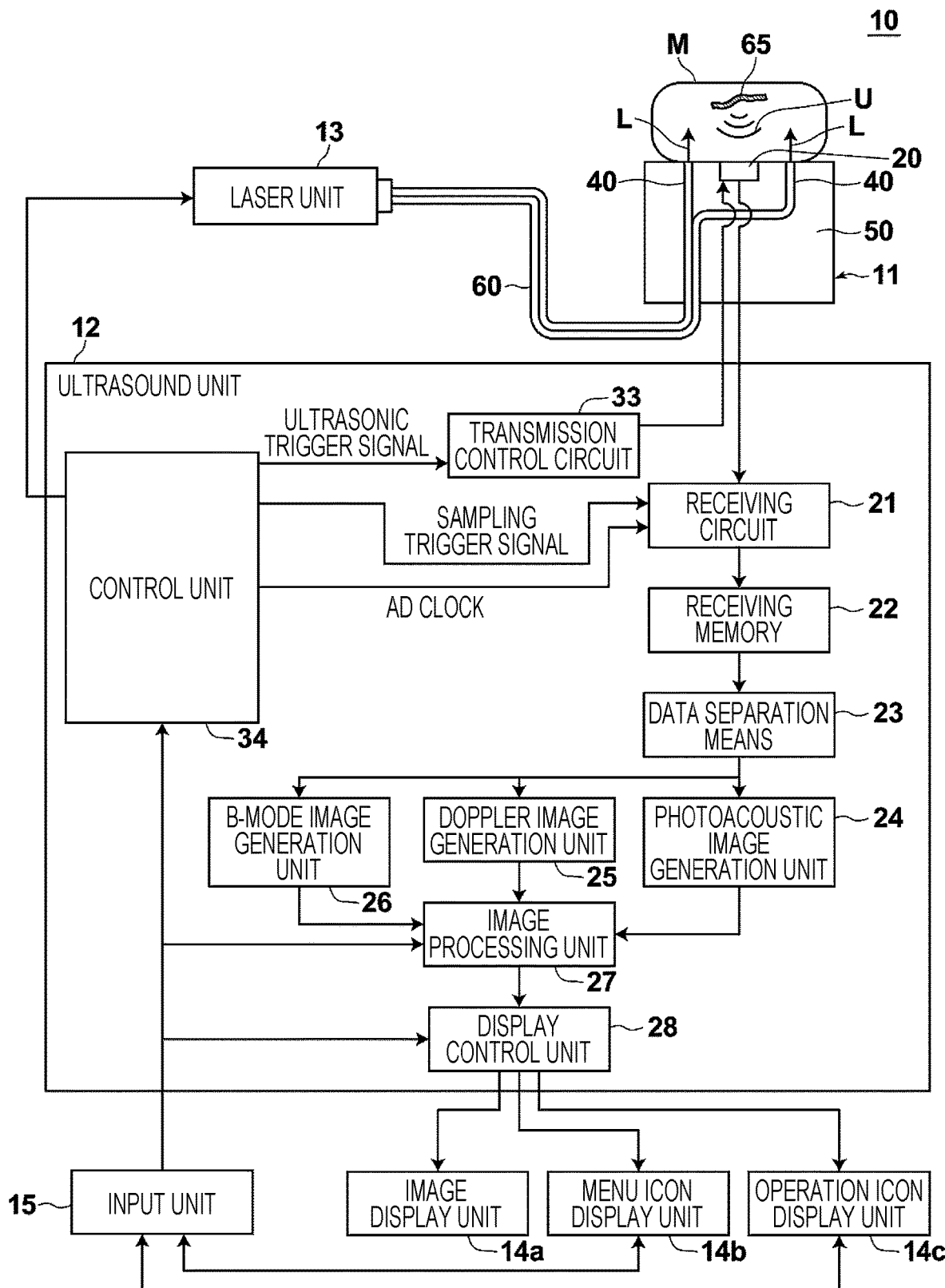
FIG. 1 is a schematic diagram illustrating an overall configuration of an acoustic wave image capturing device that performs an acoustic wave image display method according to an embodiment of the present invention.

FIG. 1 is a schematic diagram illustrating an overall configuration of an acoustic wave image capturing device 10 that performs a method for displaying an acoustic wave image according to an embodiment of the present invention. In FIG. 1, the shape of a probe 11 is schematically illustrated. By way of example, the acoustic wave image capturing device 10 according to this embodiment has a function of generating a photoacoustic image on the basis of a photoacoustic signal. As schematically illustrated in FIG. 1, the acoustic wave image capturing device 10 includes the probe 11, which is constituted by an ultrasound probe, an ultrasound unit 12, a laser unit 13, an image display unit 14a, a menu icon display unit 14b, an operation icon display unit 14c, and an input unit 15. The following sequentially describes these components.

The probe 11 has a function of emitting measurement light and ultrasonic waves to a subject M, which is, for example, a living body. The probe 11 also has a function of detecting acoustic waves U propagating within the subject M. The probe 11 emits measurement light to the subject M and detects photoacoustic waves generated within the subject from the emitted measurement light. The probe 11 further emits (transmits) ultrasonic waves (acoustic waves) to the subject M and detects (receives) reflected ultrasonic waves (reflected acoustic waves) reflected and returning from the subject M.

As used herein, the term "acoustic wave" includes an ultrasonic wave or ultrasound and a photoacoustic wave. The term "ultrasonic wave" or "ultrasound" refers to an elastic wave transmitted by a probe and a reflected wave (reflected ultrasonic wave) thereof. The term "photoacoustic wave" refers to an elastic wave generated by an absorbing body 65 absorbing measurement light. Acoustic waves emitted from the probe 11 are not limited to ultrasonic waves but may be acoustic waves of audible frequencies if appropriate frequencies are selected in accordance with the object being examined, the measurement conditions, and so on. Note that examples of the absorbing body 65 in the subject M include blood vessels and a metal member.

The probe 11 is configured as, for example, a probe supporting sector scanning, a probe supporting linear scanning, or a probe supporting convex scanning. The type of a probe used to acquire an acoustic wave image is selected as appropriate in accordance with the part to be imaged and so on. The probe 11 is connected to an optical fiber 60, which connects the laser unit 13 and the probe 11 to each other. Laser light L, which is measurement light emitted from the laser unit 13, is directed to light emission units 40 through the optical fiber 60.

The probe 11 has a transducer array 20, which is an acoustic wave detector, and the light emission units 40. In the example in FIG. 1, the probe 11 has two light emission units 40, and the two light emission units 40 are arranged at positions facing each other with the transducer array 20 interposed therebetween. The transducer array 20 and the two light emission units 40 are accommodated in a housing 50.

In this embodiment, the transducer array 20 also functions as an ultrasonic wave transmitting element. The transducer array 20 is connected to a circuit for transmitting ultrasonic waves, a circuit for receiving acoustic waves, and so on via wiring (not illustrated).

The transducer array 20 has a plurality of ultrasonic transducers arranged to be parallel in one direction. The ultrasonic transducers are electroacoustic transducer elements. The ultrasonic transducers are, for example, piezoelectric elements composed of piezoelectric ceramic. Alternatively, the ultrasonic transducers may be piezoelectric elements fabricated from polymer films such as polyvinylidene fluoride (PVDF) films. The ultrasonic transducers convert the received acoustic waves U into electrical signals. While not illustrated in FIG. 1, the probe 11 may have an acoustic lens on the subject side of the transducer array 20.

While the foregoing has described an example in which the plurality of ultrasonic transducers of the transducer array 20 are arrayed one-dimensionally, this is not meant to be limiting. The plurality of ultrasonic transducers of the transducer array 20 may be arrayed two-dimensionally.

When alternating voltages are applied to the ultrasonic transducers in the transducer array 20, the ultrasonic transducers generate ultrasonic waves of frequencies corresponding to the frequencies of the alternating voltages, and the ultrasonic waves are transmitted from the transducer array 20. Note that transmission and reception of the ultrasonic waves may be separated from each other. That is, for example, the ultrasonic waves may be transmitted from a position different from that of the probe 11 and reflected ultrasonic waves that result from the transmitted ultrasonic waves may be received by the probe 11.

The light emission units 40 emit the laser light L directed through the optical fiber 60 to the subject M. In this embodiment, the light emission units 40 are constituted by tip portions of the optical fiber 60, that is, end portions farther away from the laser unit 13 serving as a light source of the measurement light. As illustrated in FIG. 1, in this embodiment, the two light emission units 40 are located on both sides of the transducer array 20 in an elevation direction of the transducer array 20, for example, with the transducer array 20 interposed therebetween. The term "elevation direction" refers to, when the plurality of ultrasonic transducers are arrayed one-dimensionally, a direction at a right angle to the array direction and parallel to a detection surface of the transducer array 20.

Each light emission unit may include a light guide plate and a diffusion plate that are optically coupled to a tip of the optical fiber 60. As the light guide plate, for example, an acrylic plate or a quartz plate is used. As the diffusion plate, a lens diffusion plate configured such that microlenses are randomly arranged on a substrate can be used. As the lens diffusion plate, a holographic diffusion plate or an engineering diffusion plate may be used. Instead of a lens diffusion plate, for example, a quartz plate having diffusing particles dispersed thereon or the like may be used as the diffusion plate.

The laser unit 13 emits the laser light L as measurement light. The laser unit 13 includes, for example, a Q-switched flash lamp-pumped solid-state laser such as a Q-switched alexandrite laser. For example, the laser unit 13 receives a trigger signal output from a control unit 34 of the ultrasound unit 12. Upon receipt of a trigger signal, the laser unit 13 outputs the laser light L. The laser unit 13 preferably outputs pulsed laser light L having a pulse width of 1 to 100 nsec (nanoseconds).

The wavelength of the laser light L is selected as appropriate in accordance with the light absorption properties of the absorbing body 65 in the subject M to be measured. For example, when the object to be measured is hemoglobin in a living body, that is, when blood vessels are to be imaged, the wavelength of the laser light L is preferably a wavelength within a near-infrared wavelength range. The near-infrared wavelength range refers to a wavelength range of about 700 to 2500 nm. The laser light L may have any wavelength which is not limited to a wavelength within the near-infrared wavelength range. The laser unit 13 may emit the laser light L having a single wavelength or may emit the laser light L having a plurality of wavelengths. Examples of the plurality of wavelengths may include a combination of 750 nm and 800 nm. When the laser light L includes a plurality of wavelengths, beams of light of the plurality of wavelengths may be emitted simultaneously or may be switched alternately and emitted.

Note that the laser unit 13 is not limited to that including an alexandrite laser. The laser unit 13 may include, for example, a YAG-SHG (Second harmonic generation)-OPO (Optical Parametric Oscillation) laser, which is capable of outputting laser light in the near-infrared wavelength range, a YAG laser that performs no wavelength conversion, or a Ti-Sapphire (titanium-sapphire) laser. Further, the laser unit 13 is not limited to that including a flash lamp-pumped solid-state laser, but may include a laser diode pumped solid-state laser.

The optical fiber 60 directs the laser light L emitted from the laser unit 13 to the two light emission units 40. As the optical fiber 60, a well-known optical fiber such as a quartz fiber may be, but not limited to, used. As the optical fiber 60, for example, a single thick optical fiber may be used or a bundle fiber, which is made by bundling a plurality of optical fiber element wires, may be used. When a bundle fiber is used as the optical fiber 60, the laser light L enters light incident end surfaces of a plurality of optical fiber element wires collected into a single bundle. The plurality of optical fiber element wires may branch into two sections, and light-emitting ends of the two sections into which the optical fiber element wires branch may be used as the light emission units 40.

The ultrasound unit 12 includes a receiving circuit 21, a receiving memory 22, data separation means (data separation unit) 23, a photoacoustic image generation unit 24, a Doppler image generation unit 25, a B-mode image generation unit 26, an image processing unit 27, a display control unit 28, a transmission control circuit 33, and the control unit 34.

The control unit 34 controls each unit of the acoustic wave image capturing device 10. The control unit 34 includes a trigger control circuit (not illustrated). The trigger control circuit transmits an optical trigger signal to the laser unit 13 in order to acquire, for example, a photoacoustic image. Upon receipt of an optical trigger signal, the laser unit 13 turns on a flash lamp serving as an excitation source in the Q-switched solid-state laser to start excitation of a laser rod. While the laser rod is maintained in an excited state, the laser unit 13 is in a state of being able to output the laser light L.

After transmitting the optical trigger signal, the trigger control circuit of the control unit 34 transmits a Q-switch trigger signal to the laser unit 13. Upon receipt of the Q-switch trigger signal, the laser unit 13 opens a Q switch of the Q-switched solid-state laser and outputs the laser light L. The timing at which the laser unit 13 outputs the laser light L is controlled in accordance with the Q-switch trigger signal. The control unit 34 transmits the Q-switch trigger signal and further transmits a sampling trigger signal to the receiving circuit 21. The sampling trigger signal specifies the timing at which an AD converter (Analog to Digital convertor) of the receiving circuit 21 starts sampling a photoacoustic signal. The receiving circuit 21 starts sampling upon receipt of the sampling trigger signal, thereby making it possible to sample a photoacoustic signal in synchronization with the output of the laser light L.

In order to acquire an ultrasound image, the control unit 34 transmits to the transmission control circuit 33 an ultrasonic trigger signal for providing an instruction to transmit ultrasonic waves. Upon receipt of the ultrasonic trigger signal, the transmission control circuit 33 causes the probe 11 to transmit ultrasonic waves. The control unit 34 transmits a sampling trigger signal to the receiving circuit 21 in accordance with the timing of transmission of ultrasonic waves and starts sampling a reflected ultrasonic wave signal.

The receiving circuit 21 receives photoacoustic wave detection signals output from the transducer array 20 of the probe 11 and stores the received detection signals in the receiving memory 22. The receiving circuit 21 typically includes a low-noise amplifier, a variable-gain amplifier, a low-pass filter, and an AD converter. The photoacoustic wave detection signals output from the probe 11 are amplified by the low-noise amplifier and are then subjected to gain adjustment by a variable-gain amplifier in accordance with the depth. The resulting photoacoustic wave detection signals, of which the high-frequency components have been removed by the low-pass filter, are converted into digital signals by the AD converter, and the digital signals are stored in the receiving memory 22. The receiving circuit 21 is constituted by, for example, one IC (Integrated Circuit). The low-pass filter described above is provided to prevent the occurrence of folding noise during AD conversion. The cutoff frequency of the low-pass filter is typically set to a frequency that is about half the sampling frequency in AD conversion. The cutoff frequency of the low-pass filter is specifically set to about 10 MHz to 30 MHz.

In this embodiment, the probe 11 outputs photoacoustic wave detection signals and reflected ultrasonic wave detection signals. The receiving memory 22 stores digitized photoacoustic wave detection signals and reflected ultrasound detection signals. More specifically, the photoacoustic wave detection signals described above are signals obtained by detecting photoacoustic waves generated from within the subject M which has received the laser light L emitted to the subject M. In contrast, the reflected ultrasound detection signals described above are signals obtained by detecting reflected acoustic waves, which are ultrasonic waves, or acoustic waves, emitted to the subject M and reflected within the subject M. The data separation means 23 reads out data for a photoacoustic image, that is, the digitized photoacoustic wave detection signals, from the receiving memory 22 and transmits the photoacoustic wave detection signals to the photoacoustic image generation unit 24. Further, the data separation means 23 reads out data for a reflected ultrasound image, that is, the digitized reflected ultrasound detection signals, from the receiving memory 22 and transmits the reflected ultrasound detection signals to the Doppler image generation unit 25 or the B-mode image generation unit 26.

The photoacoustic image generation unit 24 reconstructs the photoacoustic wave detection signals received from the receiving memory 22 via the data separation means 23 and generates a photoacoustic image. Specifically, the photoacoustic image generation unit 24 adds together photoacoustic wave detection signals based on signals output from the individual ultrasonic transducers of the transducer array 20 at delay times corresponding to the respective positions of the ultrasonic transducers and generates a photoacoustic wave detection signal for one line (delay-and-sum method).

The photoacoustic image generation unit 24 may perform reconstruction by using the CBP method (Circular Back Projection) instead of using the delay-and-sum method. Alternatively, the photoacoustic image generation unit 24 may perform reconstruction by using Hough transformation or Fourier transformation. Reconstructed photoacoustic wave detection signals for a plurality of lines undergo signal processing such as detection processing and log conversion processing and are then sent to the display control unit 28 via the image processing unit 27 as signals for displaying a photoacoustic image (tomographic image) for a certain cross section of the subject M.

The B-mode image generation unit 26 performs processing, which is basically similar to that for the photoacoustic wave detection signals described above, on the reflected ultrasound detection signals received from the receiving memory 22 via the data separation means 23 to generate reflected ultrasound detection signals for a plurality of lines indicating an ultrasound image (tomographic image). The reflected ultrasound detection signals generated in this way are sent to the display control unit 28 via the image processing unit 27 as signals for displaying an ultrasound B-mode image (hereinafter referred to simply as a B-mode image) for a certain cross section of the subject M.

The Doppler image generation unit 25 performs frequency analysis of velocity information from the reflected ultrasound detection signals received from the receiving memory 22 via the data separation means 23, extracts blood flow, tissues, and/or contrast medium echo components by using the Doppler effect, and generates a color Doppler image signal for displaying a color Doppler image indicating, for example, blood flow portions. The color Doppler image signal is also sent to the display control unit 28 via the image processing unit 27.

The Doppler image generation unit 25 is also capable of generating so-called color flow mapping data, which represents the spatial distributions of average velocity, variance, power, and/or the like of blood flow in color, on the basis of the extracted blood flow, tissues, and/or contrast medium echo components based on the Doppler effect. Based on such color flow mapping data, a color flow map in which the spatial distributions of average velocity, variance, power, and/or the like of blood flow are separated by color or displayed in a single color with different brightness and/or saturation levels can be displayed on the image display unit 14a.

The Doppler image generation unit 25 may also create an image indicating the two-dimensional distributions of power in a Doppler signal. A power Doppler image is typically an image in which the power distributions of power in a Doppler signal are separated by color or displayed in a single color with different brightness and/or saturation levels.

The display control unit 28 causes the image display unit 14a to display a photoacoustic image on the basis of the signals described above for displaying a photoacoustic image. Further, the display control unit 28 causes the image display unit 14a to display a B-mode image on the basis of the signals for displaying an ultrasound B-mode image described above and causes the image display unit 14a to display a color Doppler image on the basis of the color Doppler image signal. These three types of images are separately displayed on the image display unit 14a or are combined into a composite image which is displayed on the image display unit 14a. In the latter case, for example, the display control unit 28 superimposes the photoacoustic image and the B-mode image on each other to combine the images. When the photoacoustic image and the B-mode image are displayed superimposed on each other, a portion of the photoacoustic image that cannot be imaged can be observed in the B-mode image.

Additionally, all of the three types of images described above can be combined into an image and the image can be displayed on the image display unit 14a. In this case, the composite image of the photoacoustic image and the B-mode image, described above, is overlaid with the color Doppler image in which blood flow portions of the subject M, which is, for example, a living body, are displayed in color. Instead of the color Doppler image, the color flow map described above can be displayed.

Note that the three types of acoustic wave images described above are acquired with time intervals. In order to display these acoustic wave images in a superimposed manner, for example, the display control unit 28 includes a buffer memory for temporarily storing an image signal indicating each image.

Next, the display of the photoacoustic image, the Doppler image, and the B-mode image, described above, will be described in more detail. While the following describes the display of three types of acoustic wave images acquired in the acoustic wave image capturing device 10, this is not meant to be limiting. The present invention is also applicable to a case in which an acquired image is temporarily stored in, for example, storage means (storage unit) constituting a database and then the image, which is read from the storage means, is displayed.

Figure 2:
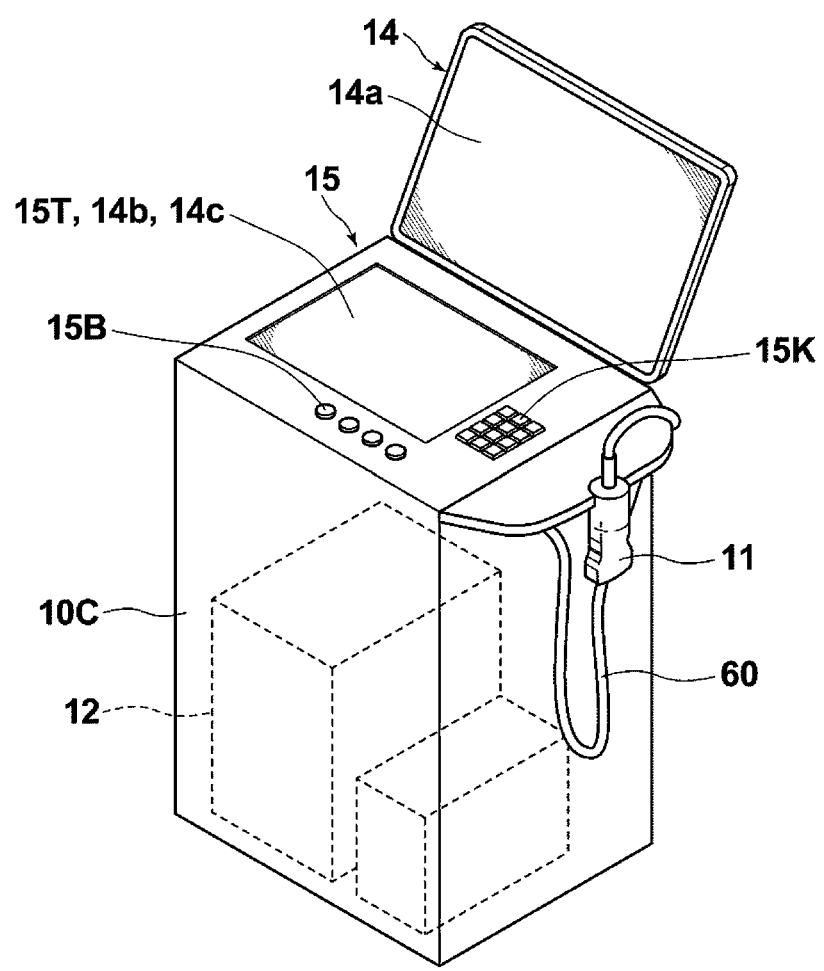
FIG. 2 is a perspective view illustrating the acoustic wave image capturing device.

The image display unit 14a serving as image display unit, the menu icon display unit 14b serving as menu icon display unit, and the operation icon display unit 14c and the input unit 15 serving as operation icon display unit, which are illustrated in FIG. 1, are constituted by a well-known computer system together with the ultrasound unit 12 illustrated in the same figure. FIG. 2 is a perspective view illustrating the acoustic wave image capturing device 10. The acoustic wave image capturing device 10 includes the image display unit 14a, the menu icon display unit 14b, the operation icon display unit 14c, and the input unit 15. In FIG. 2, elements equivalent to those in FIG. 1 described previously are assigned the same numerals, and a description thereof is omitted if not necessary in particular (this also applies to the following).

The acoustic wave image capturing device 10 is configured as a so-called tower type device, as an example. A housing 10C houses the ultrasound unit 12 and the laser unit 13. More specifically, the image display unit 14a is an image display screen of an image display device 14 constituted by, for example, a liquid crystal display device or the like. The input unit 15 is constituted by, for example, one touch panel 15T, a plurality of input buttons 15B, a plurality of input keys 15K, and so on. The image display unit 14a and the touch panel 15T are each configured to be able to display a color image.

In this embodiment, the touch panel 15T, which also includes an input function, is used as the menu icon display unit 14b and the operation icon display unit 14c illustrated in FIG. 1. That is, the menu icon display unit 14b and the operation icon display unit 14c constitute part of the input unit 15. While the menu icon display unit 14b and the operation icon display unit 14c are part of the input unit 15, the menu icon display unit 14b and the operation icon display unit 14c are identified separately from the input unit 15 in FIG. 1, for sake of convenience.

Figure 3:
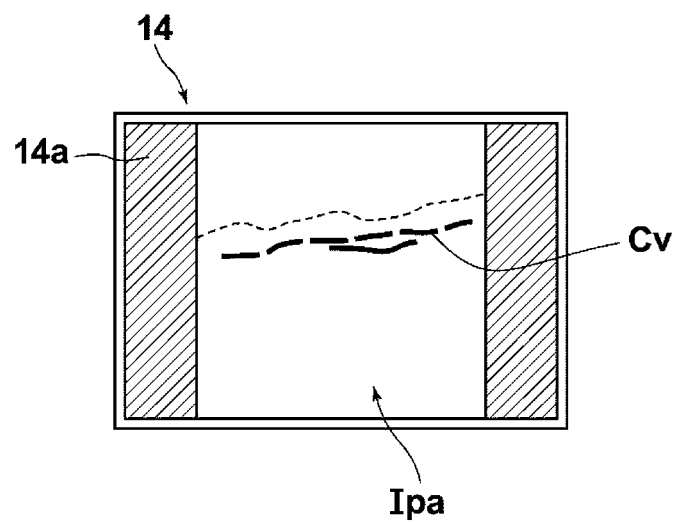
FIG. 3 is a schematic diagram illustrating an example of an acoustic wave image.
Figure 4:
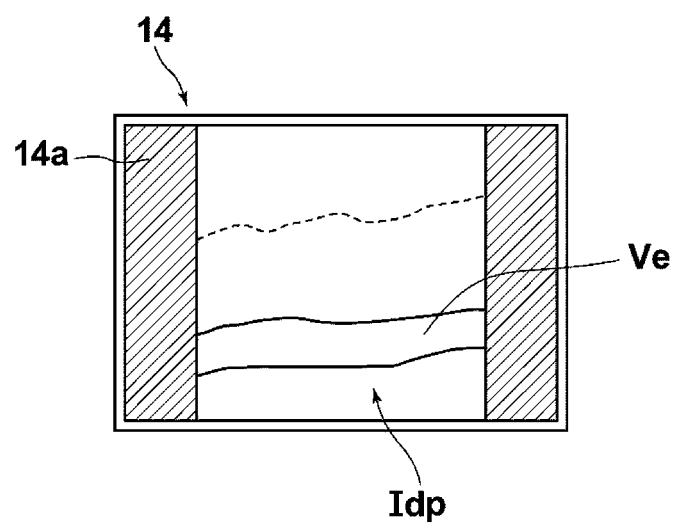
FIG. 4 is a schematic diagram illustrating another example of the acoustic wave image.
Figure 5:
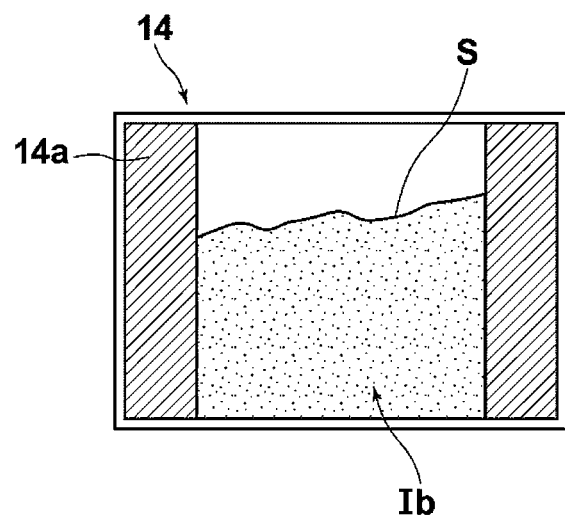
FIG. 5 is a schematic diagram illustrating still another example of the acoustic wave image.

FIG. 3, FIG. 4, and FIG. 5 schematically illustrate states in which an example of the photoacoustic image, an example of the Doppler image, and an example of the B-mode image are individually displayed on the image display unit 14a of the image display device 14, respectively. In the following, the photoacoustic image is represented by Ipa, the Doppler image is represented by Idp, and the B-mode image is represented by Ib. Furthermore, the photoacoustic image Ipa is considered to be a first acoustic wave image, the Doppler image Idp is considered to be a second acoustic wave image, and the B-mode image Ib is considered to be a third acoustic wave image.

As illustrated in FIG. 3, the photoacoustic image Ipa shows a blood vessel Cv and so on present in a portion comparatively close to a skin surface S. As illustrated in FIG. 4, the Doppler image Idp shows a blood flow portion Ve and so on located at positions deeper than the position of the blood vessel Cv. As illustrated in FIG. 5, the B-mode image Ib shows a tomographic cross section extending from the skin surface S of the subject M (see FIG. 1), which is, for example, a living body, to the inside.

The Doppler image Idp is, for example, a color Doppler image. In a color Doppler image, in most cases, a blood flow portion Ve flowing in a direction toward the probe 11 (see FIG. 1) is displayed in a single warm color, whereas a blood flow portion Ve flowing in a direction away from the probe 11 is displayed in a single cold color.

Instead of or in addition to the display of a color Doppler image as the Doppler image Idp, a color flow map or a power Doppler image can be displayed as the Doppler image Idp. Furthermore, instead of the Doppler image Idp or in addition to a color Doppler image, an elastography image may be displayed.

Figure 6:
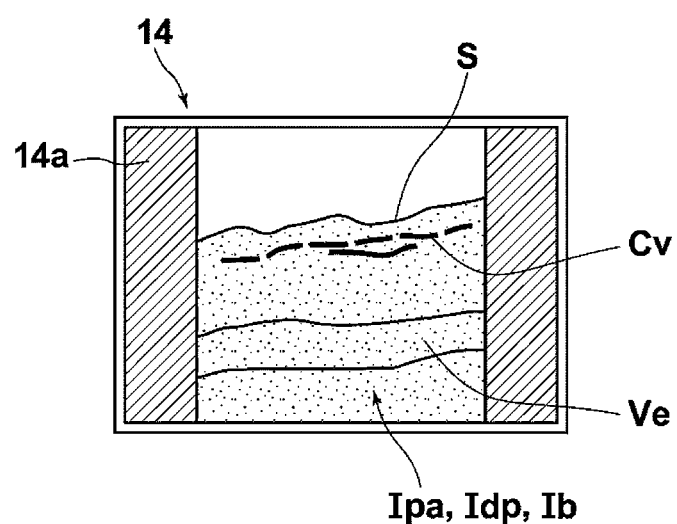
FIG. 6 is a schematic diagram illustrating still another example of the acoustic wave image.

FIG. 6 illustrates an example in which the three types of images Ipa, Idp and Ib illustrated in FIGS. 3 through 5 are displayed superimposed on one another on the image display unit 14a. In the superimposed display, the three types of images are overlaid on one another in the order of the photoacoustic image Ipa, the Doppler image Idp, and the B-mode image Ib as viewed from, for example, the image observer side (the close side). In this specification, the expression "close side" or "far side" regarding the display order of acoustic wave images to be displayed on top of one another refers to the "close side" or "far side" as viewed from the image observer side unless otherwise stated in particular.

The display control unit 28 illustrated in FIG. 1 controls the superimposed display described above. The display control unit 28 functions as an image display control unit that performs all types of control regarding image display including superimposed display control. Further, the display control unit 28 also functions as a menu icon display control unit that performs control to display menu icons on the menu icon display unit 14b, as described below, and also functions as an operation icon display control unit that performs control to display operation icons on the operation icon display unit 14c.

The image processing unit 27 performs various types of processing (image processing) on the photoacoustic image Ipa, the Doppler image Idp, and the B-mode image Ib. The following describes the selection of an image to be processed and the selection of a process when the image processing unit 27 is to perform the process.

Figure 7:
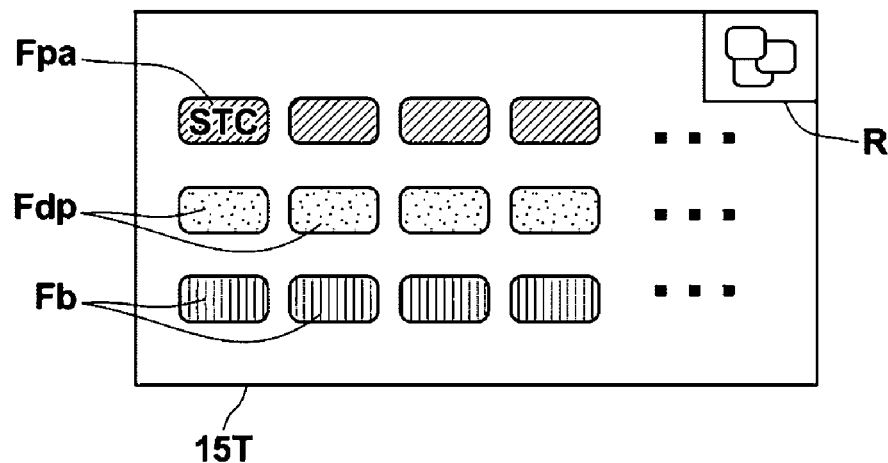
FIG. 7 is a schematic diagram illustrating an example of menu icons.

The touch panel 15T illustrated in FIG. 2 also functions as the menu icon display unit 14b. As illustrated in FIG. 7, a plurality of photoacoustic-image menu icons Fpa, a plurality of Doppler-image menu icons Fdp, and a plurality of B-mode-image menu icons Fb are displayed on a display screen of the touch panel 15T. The plurality of photoacoustic-image menu icons Fpa are laterally arranged in a line.

The plurality of Doppler-image menu icons Fdp are laterally arranged in a line, and the plurality of B-mode-image menu icons Fb are laterally arranged in a line. In the following, as appropriate, the plurality of photoacoustic-image menu icons Fpa are referred to as a first menu icon group, the plurality of Doppler-image menu icons Fdp are referred to as a second menu icon group, and the plurality of B-mode-image menu icons Fb are referred to as a third menu icon group.

As illustrated in FIG. 7, the plurality of photoacoustic-image menu icons Fpa, the plurality of Doppler-image menu icons Fdp, and the plurality of B-mode-image menu icons Fb are arranged in separate groups. The term "in separate groups", as used herein, indicates that menu icons in a certain group are collected and arranged at positions clearly distinguishable from the menu icons in the other groups.

Note that an operation icon display region R that shows a plurality of operation icons is provided in a portion (the upper right corner in FIG. 7) of the touch panel 15T. The operation icons will be described below.

Each of the plurality of photoacoustic-image menu icons Fpa is an icon for designating a predetermined process to be performed on the photoacoustic image Ipa. Each of the plurality of Doppler-image menu icons Fdp is an icon for designating a predetermined process to be performed on the Doppler image Idp. Each of the plurality of B-mode-image menu icons Fb is an icon for designating a predetermined process to be performed on the B-mode image Ib. Examples of the predetermined process to be performed on each image include amplification, dynamic range adjustment, STC (Sensitivity Time gain Control), echo enhancement, noise removal processing, and blurring processing.

Each menu icon is preferably displayed so as to identify a process to be designated. For example, if a process designated using a certain photoacoustic-image menu icon Fpa included in the first menu icon group is an STC process, as exemplarily illustrated in FIG. 7, the photoacoustic-image menu icon Fpa is preferably displayed with "STC".

For example, consideration is given to a case where the photoacoustic image Ipa, the Doppler image Idp, and the B-mode image Ib are overlaid on one another in a superimposed image in this order from the close side. In this case, it is preferable that the plurality of photoacoustic-image menu icons Fpa, the plurality of Doppler-image menu icons Fdp, and the plurality of B-mode-image menu icons Fb be arranged in the order corresponding to the display order (stacking order) of the three types of acoustic wave images in the superimposed image. For example, it is preferable that the display order of the photoacoustic image Ipa, the Doppler image Idp, and the B-mode image Ib in the superimposed image in a direction from the close side to the far side and the display order of the first menu icon group, the second menu icon group, and the third menu icon group on the display screen of the touch panel 15T in a direction from the top to the bottom of the screen coincide with each other. In this case, the device user is able to intuitively identify associations between the images Ipa, Idp, and Ib and the menu icons Fpa, Fdp, and Fb.

In addition, the three types of acoustic wave images to be superimposed on one another in the superimposed image are preferably assigned different display colors. For example, in the superimposed image, the photoacoustic image Ipa is displayed in red, the Doppler image Idp is displayed in yellow, and the B-mode image Ib is displayed in gray. In this case, it is preferable that the menu icons corresponding to each image be displayed in the same display color as the display color of the image. For example, in the example described above, it is preferable that the photoacoustic-image menu icons Fpa be displayed in red, the Doppler-image menu icons Fdp be displayed in yellow, and the B-mode-image menu icons Fb be displayed in gray. Display in corresponding colors allows the device user to intuitively identify associations between the images Ipa, Idp, and Ib and the menu icons Fpa, Fdp, and Fb, in terms of a different viewpoint from the display order.

As described above, the expression "the display color of an image and the display color of menu icons are identical" is used to also include a case where both display colors are slightly different from each other due to the difference in performance between the image display device 14 and the touch panel 15T. This also applies to the other combinations regarding the two display colors.

Note that it is not always necessary to associate the display color of menu icons with the display color of a displayed image, as described above.

When any one menu icon is operated on the touch panel 15T, information identifying a process designated by the operation of the menu icon is transmitted to the image processing unit 27. For example, when the device user presses any one of the photoacoustic-image menu icons Fpa on the touch panel 15T, the designation of a process indicated by the menu icon for the photoacoustic image Ipa is transmitted to the image processing unit 27. In this case, the image processing unit 27 performs the designated process on a signal indicating the photoacoustic image Ipa. The image display unit 14a displays a photoacoustic image on which the designated process has been performed.

Likewise, when the device user presses any one of the Doppler-image menu icons Fdp on the touch panel 15T, the designation of a process indicated by the menu icon for the Doppler image Idp is transmitted to the image processing unit 27. The image processing unit 27 performs the designated process on a signal indicating the Doppler image Idp, and the image display unit 14a displays a Doppler image on which the designated process has been performed. When the device user presses any one of the B-mode-image menu icons Fb on the touch panel 15T, the designation of a process indicated by the menu icon for the B-mode image Ib is transmitted to the image processing unit 27. The image processing unit 27 performs the designated process on a signal indicating the B-mode image Ib, and the image display unit 14a displays a B-mode image on which the designated process has been performed.

While FIG. 1 illustrates an example in which the image processing unit 27 is provided in a stage subsequent to the photoacoustic image generation unit 24, the Doppler image generation unit 25, and the B-mode image generation unit 26, the position at which the image processing unit 27 is arranged is not limited thereto. The image processing unit 27 may be arranged in a preceding stage of these image generation units and perform processes on signals input to the image generation units. Alternatively, the image processing unit 27 may be arranged in each of the image generation units and perform signal processing on a signal being subjected to image generation in the image generation unit.

In this embodiment, the stacking order of the photoacoustic image Ipa, the Doppler image Idp, and the B-mode image Ib can be changed using the first menu icon group, the second menu icon group, and the third menu icon group. The following describes this point.

On the touch panel 15T, the menu icons Fpa, Fdp, and Fb can be dragged and dropped with a finger of the user or the like. The operation of dragging and dropping is not limited to operating a touch panel with a finger. For example, in a configuration in which the menu icon display unit 14b is included in a display device different from the touch panel 15T, the device user may perform a drag-and-drop operation using, for example, input means (input unit) such as a mouse.

Figure 8:
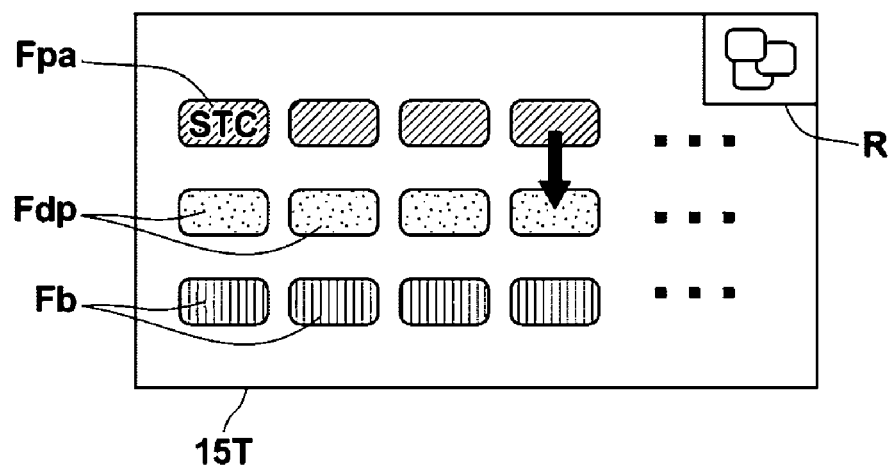
FIG. 8 is a schematic diagram illustrating another state of the menu icons in FIG. 7.

FIG. 8 illustrates another state of the menu icons in FIG. 7. For example, the device user drags and drops one of the photoacoustic-image menu icons Fpa included in the first menu icon group displayed in the top row onto one of the Doppler-image menu icons Fdp in a way indicated by a thick arrow in FIG. 8. When an operation of dragging and dropping is performed, it is preferable that the display order of the menu icon groups in the direction from the top to the bottom on the touch panel 15T be changed in accordance with the drag-and-drop operation.

Figure 9:
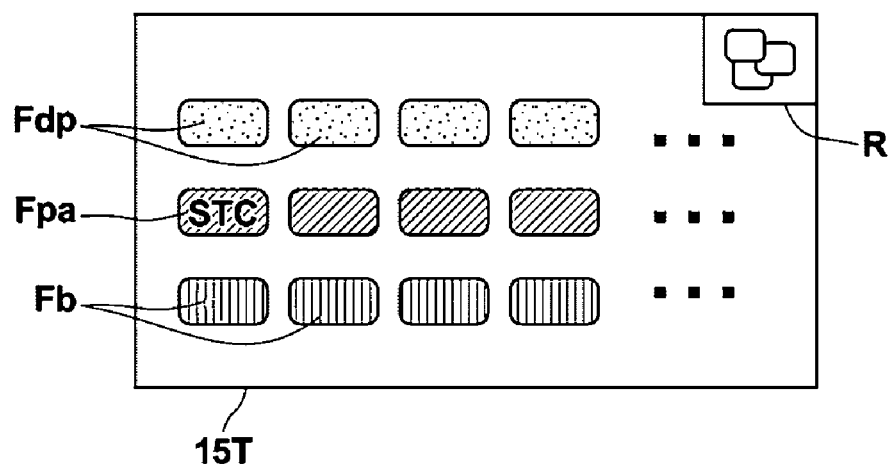
FIG. 9 is a schematic diagram illustrating still another state of the menu icons in FIG. 7.

FIG. 9 illustrates the state of the menu icons after the drag-and-drop operation is performed. When the device user drags and drops one of the photoacoustic-image menu icons Fpa onto one of the Doppler-image menu icons Fdp, as illustrated in FIG. 9, the plurality of photoacoustic-image menu icons Fpa, which are arranged side-by-side in the top row, are moved to the positions in the second row, and the plurality of Doppler-image menu icons Fdp, which are arranged side-by-side at the positions in the second row, are moved to the positions in the top row.

When the display order of the menu icon groups is changed on the touch panel 15T, it is preferable that the display order of the photoacoustic image Ipa, the Doppler image Idp, and the B-mode image Ib in the superimposed image be changed in accordance with the changed display order of the menu icon groups. For example, as in the example described above, when the photoacoustic-image menu icons Fpa and the Doppler-image menu icons Fdp are interchanged in the display order, it is preferable that the display order of the photoacoustic image Ipa and the Doppler image Idp in the superimposed image displayed on the image display unit 14a be changed accordingly. Specifically, it is preferable that the display order in the superimposed image displayed on the image display unit 14a be changed such that the Doppler image Idp is displayed closest to the image observer side and the photoacoustic image Ipa is displayed behind the Doppler image Idp. Since no change is made to the display order of the B-mode-image menu icons Fb, the display order of the B-mode image Ib, which is displayed farthest from the image observer side in the superimposed image, is not changed.

In this embodiment, the display control unit 28 (see FIG. 1) performs control to change the display positions of the photoacoustic-image menu icons Fpa and the Doppler-image menu icons Fdp and change the stacking order (display order) of the photoacoustic image Ipa and the Doppler image Idp on the basis of a signal input from the touch panel 15T also acting as an input unit. The display control unit 28 functions as a menu icon display control unit and also functions as an image display control unit.

When there is a correspondence between the display order of the first menu icon group, the second menu icon group, and the third menu icon group and the display order of the photoacoustic image, the Doppler image, and the B-mode image, which are displayed superimposed on one another, and when the display order of the menu icon groups is changed, it is preferable that the display order of the photoacoustic image, the Doppler image, and the B-mode image, which are displayed superimposed on one another, be changed in accordance with the change in the display order of the menu icon groups. In this case, an advantage that the device user is able to intuitively identify associations between the images Ipa, Idp, and Ib and the menu icons Fpa, Fdp, and Fb, is still maintained.

While the foregoing has described an example in which one of the photoacoustic-image menu icons is dragged and dropped onto one of the Doppler-image menu icons, this is not meant to be limiting. For example, one of the Doppler-image menu icons Fdp may be dragged and dropped onto one of the photoacoustic-image menu icons Fpa. Also in this case, the photoacoustic-image menu icons and the Doppler-image menu icons are interchanged in the display order, and the photoacoustic image and the Doppler image in the superimposed image are also interchanged in the display order.

The menu icons Fpa, Fdp, and Fb may be displayed in any other form. The following describes another form with reference to FIG. 10 to FIG. 14. In this example, the menu icons Fpa, Fdp, and Fb are displayed in a manner similar to that of the display style of worksheets in spreadsheet software, "Excel" (registered trademark).

Figure 10:
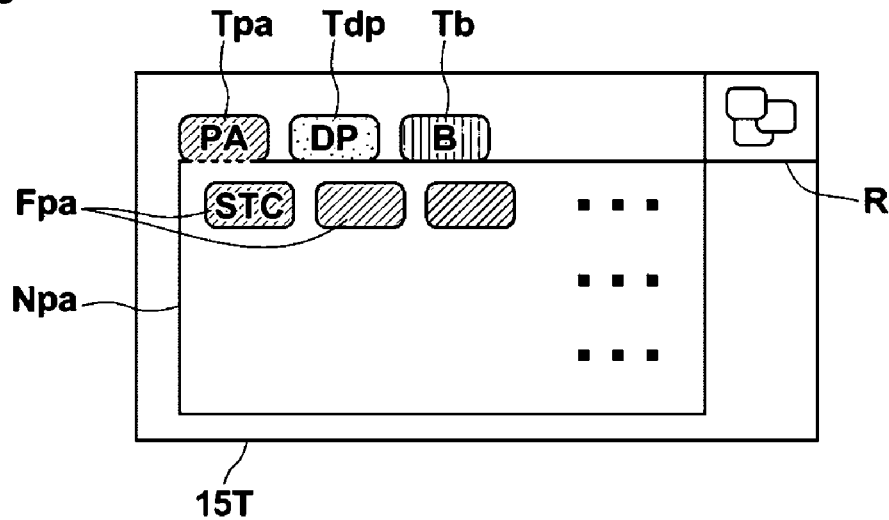
FIG. 10 is a schematic diagram illustrating another example of the menu icons.
Figure 11:
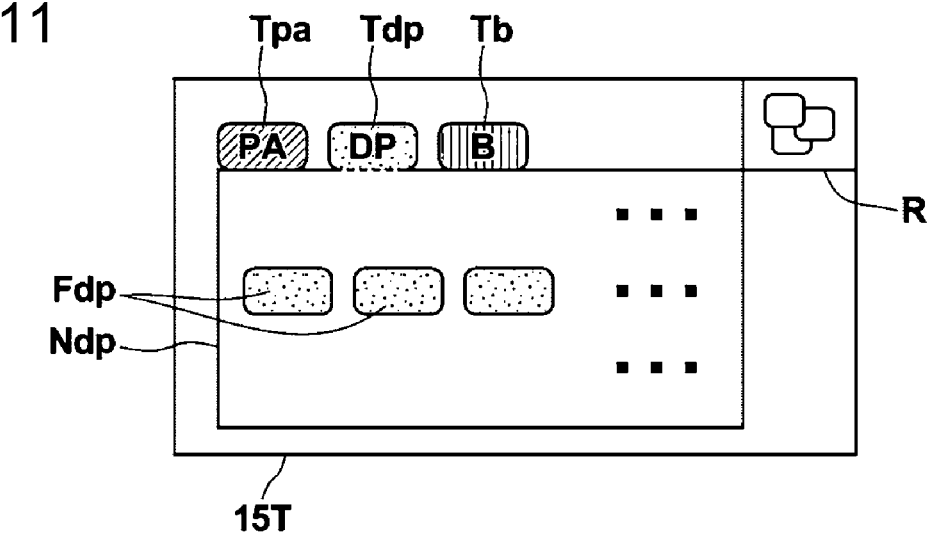
FIG. 11 is a schematic diagram illustrating another state of the menu icons in FIG. 10.
Figure 12:
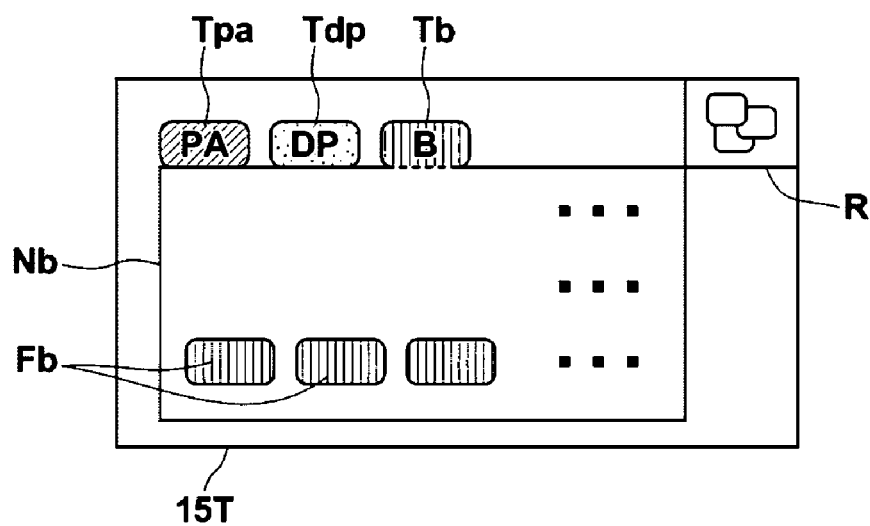
FIG. 12 is a schematic diagram illustrating still another state of the menu icons in FIG. 10.

That is, as illustrated in FIG. 10 to FIG. 12, a first menu sheet Npa, a second menu sheet Ndp, and a third menu sheet Nb are selectively displayed on the touch panel 15T. On the first menu sheet Npa, the photoacoustic-image menu icons Fpa for designating a process to be performed on the photoacoustic image Ipa are displayed laterally side-by-side in a line. On the second menu sheet Ndp, the Doppler-image menu icons Fdp for designating a process to be performed on the Doppler image Idp are displayed laterally side-by-side in a line. On the third menu sheet Nb, the B-mode-image menu icons Fb for designating a process to be performed on the B-mode image Ib are displayed laterally side-by-side in a line.

Also in this example, the plurality of photoacoustic-image menu icons Fpa, the plurality of Doppler-image menu icons Fdp, and the plurality of B-mode-image menu icons Fb are arranged in separate groups.

For example, a first selection tab Tpa illustrated in FIG. 10 is a tab corresponding to the first menu sheet Npa. For example, a second selection tab Tdp illustrated in FIG. 11 is a tab corresponding to the second menu sheet Ndp. For example, a third selection tab Tb illustrated in FIG. 12 is a tab corresponding to the third menu sheet Nb. When the first selection tab Tpa is touched on the touch panel 15T, the first menu sheet Npa is displayed (see FIG. 10). When the second selection tab Tdp is touched, the second menu sheet Ndp is displayed (see FIG. 11), and when the third selection tab Tb is touched, the third menu sheet Nb is displayed (see FIG. 12).

In this example, when a selection tab is touched, a menu sheet corresponding to the touched selection tab is displayed. The first menu sheet Npa, the second menu sheet Ndp, or the third menu sheet Nb is selectively displayed in accordance with a touched selection tab to select an image to be processed. In addition, the photoacoustic-image menu icons Fpa, the Doppler-image menu icons Fdp, or the B-mode-image menu icons Fb displayed in each menu sheet are used to designate a process to be performed on the image selected as an object to be processed.

Also in this example, it is preferable that the photoacoustic-image menu icons Fpa be displayed in the same display color as that of the photoacoustic image Ipa, the Doppler-image menu icons Fdp be displayed in the same display color as that of the Doppler image Idp, and the B-mode-image menu icons Fb be displayed in the same display color as that of the B-mode image Ib. In this example, it is also preferable that the order of arrangement (display order) of the first selection tab Tpa for selecting the first menu sheet Npa, the second selection tab Tdp for selecting the second menu sheet Ndp, and the third selection tab Tb for selecting the third menu sheet Nb, which is related to a predetermined direction (the left-to-right direction on the touch panel 15T), be associated with the display order of the photoacoustic image Ipa, the Doppler image Idp, and the B-mode image Ib, which are displayed on top of one another in the superimposed image.

The configuration described above allows the device user to intuitively identify associations between the images Ipa, Idp, and Ib and the respective menu sheets (i.e., the icons Fpa, Fdp, and Fb on the menu sheets).

In this example, it is preferable that the entirety of the first menu sheet Npa be displayed in the same color as that of the photoacoustic-image menu icons Fpa, the entirety of the second menu sheet Ndp be displayed in the same color as that of the Doppler-image menu icons Fdp, and the entirety of the third menu sheet Nb be displayed in the same color as that of the B-mode-image menu icons Fb.

In this example, it is preferable that the display order of the photoacoustic image Ipa, the Doppler image Idp, and the B-mode image Ib in the superimposed image be changed using the first selection tab Tpa, the second selection tab Tdp, and the third selection tab Tb. The following describes this point.

In this example, any one of the menu sheets Npa, Ndp and Nb is selectively displayed in accordance with a touch of a selection tab. The display order of the first selection tab Tpa, the second selection tab Tdp, and the third selection tab Tb, which is related to a predetermined direction, corresponds to the display order of the photoacoustic image Ipa, the Doppler image Idp, and the B-mode image Ib in the superimposed image.

The device user is able to perform a drag-and-drop operation of the first selection tab Tpa, the second selection tab Tdp, and the third selection tab Tb on the touch panel 15T with their finger or the like. The drag-and-drop operation of the selection tabs may also be performed using, for example, input means such as a mouse in a way similar to that of the dragging and dropping of the menu icons described above.

Figure 13:
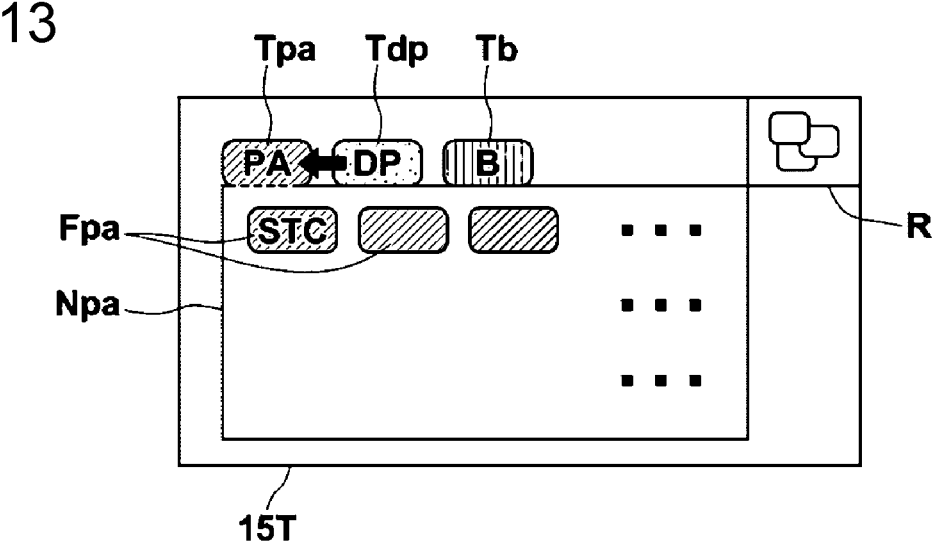
FIG. 13 is a schematic diagram illustrating still another state of the menu icons in FIG. 10.

FIG. 13 illustrates another state of the menu icons in FIG. 10. As indicated by a thick arrow in FIG. 13, for example, the device user drags and drops the second selection tab Tdp displayed at the center in the left-right direction for displaying the Doppler-image menu icons Fdp onto the first selection tab Tpa for displaying the photoacoustic-image menu icons Fpa.

Figure 14:
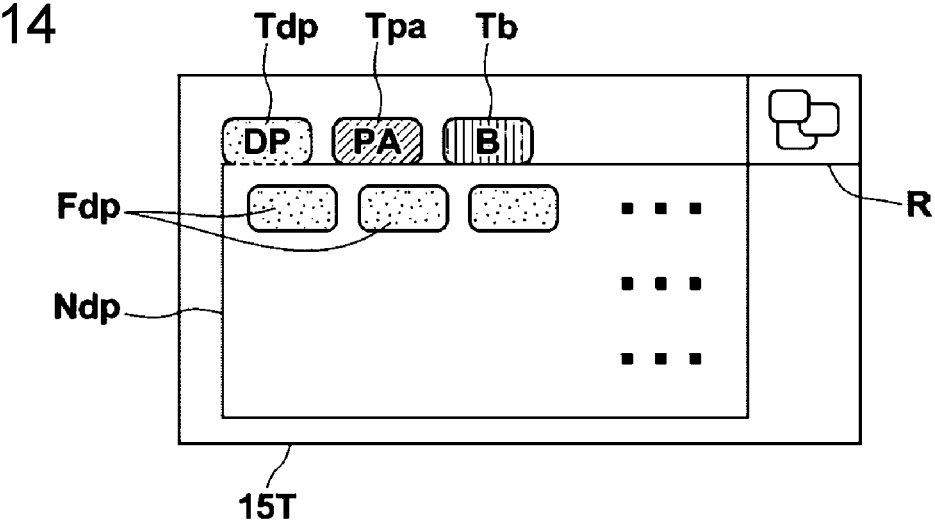
FIG. 14 is a schematic diagram illustrating still another state of the menu icons in FIG. 10.

FIG. 14 illustrates the display state of menu icons after the drag-and-drop operation is performed. When the device user drags and drops the second selection tab Tdp onto the first selection tab Tpa, as illustrated in FIG. 14, the second selection tab Tdp, which is displayed at the second position from the left of the touch panel 15T, is moved to the first position from the left, and the first selection tab Tpa, which is displayed at the first position from the left, is moved to the second position from the left. In this case, it is preferable that the display order of the acoustic wave images in the superimposed image be changed in accordance with the change in the display order of the selection tabs. For example, it is preferable that a superimposed image in which the photoacoustic image, the Doppler image, and the B-mode image are overlaid on one another in this display order from the close side be changed to a superimposed image in which the Doppler image, the photoacoustic image, and the B-mode image are overlaid on one another in this display order from the close side.

In this embodiment, the display control unit 28 (see FIG. 1) performs control to change the display positions of the first selection tab Tpa and the second selection tab Tdp and change the stacking order of the photoacoustic image Ipa and the Doppler image Idp on the basis of a signal output from the touch panel 15T also acting as an input unit. Also in this case, the display control unit 28 functions as a menu icon display control unit and also functions as an image display control unit.

Also in this example, an advantage that the device user is able to intuitively identify associations between the images Ipa, Idp, and Ib and the respective menu sheets (i.e., the icons Fpa, Fdp, and Fb on the menu sheets) is still maintained.

While the foregoing has described an example in which the second selection tab Tdp is dragged and dropped onto the first selection tab Tpa, this is not meant to be limiting. For example, the first selection tab Tpa may be dragged and dropped onto the second selection tab Tdp. Also in this case, as in the foregoing, the first selection tab and the second selection tab are interchanged in the display order, and the photoacoustic image and the Doppler image in the superimposed image are interchanged in the display order.

If the stacking order of the photoacoustic image Ipa, the Doppler image Idp, and the B-mode image Ib can be changed, an image on the close side may hide image(s) therebehind or the image(s) may be difficult to view depending on the colors of the images. For example, when the photoacoustic image Ipa displayed in red is overlaid with the B-mode image Ib displayed in gray such that the B-mode image Ib appears to be behind the photoacoustic image Ipa, the B-mode image Ib is invisible or is difficult to view.

To address the issue described above, in this embodiment, a display image selected using the first selection tab Tpa, the second selection tab Tdp, or the third selection tab Tb can be made to appear transparent so that display images behind the display image can be seen. That is, in the example described above, a "double-click" operation is applied to the first selection tab Tpa as an example of a predetermined operation. The double-click operation can be performed with a finger of the user, for example, when the touch panel 15T illustrated in FIG. 10 to FIG. 14 is used as the menu icon display unit 14b (see FIG. 1 and FIG. 2). Alternatively, the double-click operation can be performed using input means such as a mouse.

When the double-click operation described above is performed, the first selection tab Tpa displayed in red is displayed in a transparent manner. Additionally, the photoacoustic image Ipa, for which a process is designated using the menu icons Fpa in the menu sheet Npa corresponding to the first selection tab Tpa, is also displayed as transparent red on the image display unit 14a. Thus, the B-mode image Ib displayed in gray can be seen without being hidden by the photoacoustic image Ipa.

The first selection tab Tpa and the photoacoustic image Ipa displayed in a transparent manner may be displayed in a substantially fully transparent manner or in a semi-transparent manner.

Figure 19:
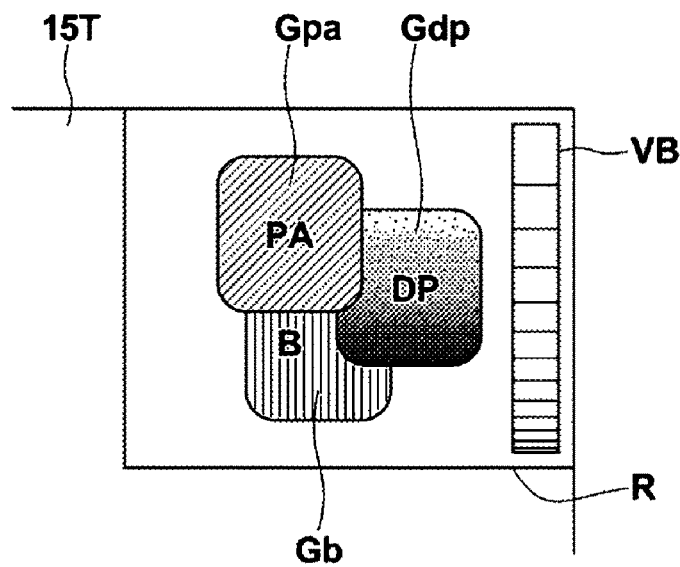
FIG. 19 is a schematic diagram illustrating still another state of the operation icons in FIG. 15.

When the double-click operation described above is performed, a gradation bar may be displayed on the touch panel 15T. For example, a gradation bar VB illustrated in FIG. 19 is displayed at any position on a display screen. The device user touches or clicks a desired position on the gradation bar VB. It is desirable that the display of the first selection tab Tpa and the photoacoustic image Ipa in a transparent manner be adjustable in accordance with the touched position on the gradation bar VB.

The foregoing has described a point in which processes designated using the menu icons Fpa, Fdp, and Fb are performed on the photoacoustic image Ipa, the Doppler image Idp, and the B-mode image Ib, respectively, and also describes an attached function related to the menu icons Fpa, Fdp, and Fb. The following describes operation icons for implementing a further enhanced function.

The operation icons for implementing a further enhanced function are displayed in, for example, the operation icon display region R illustrated in FIG. 7 to FIG. 14. FIG. 15 to FIG. 21 schematically illustrate the operation icons. In this embodiment, a photoacoustic-image operation icon (first operation icon) Gpa related to the display of the photoacoustic image Ipa, a Doppler-image operation icon (second operation icon) Gdp related to the display of the Doppler image Idp, and a B-mode-image operation icon (third operation icon) Gb related to the display of the B-mode image Ib are displayed.

The photoacoustic-image operation icon Gpa, the Doppler-image operation icon Gdp, and the B-mode-image operation icon Gb are displayed in a portion of the touch panel 15T functioning as the operation icon display unit 14c illustrated in FIG. 1. In this example, a portion of the Doppler-image operation icon Gdp and a portion of the B-mode-image operation icon Gb are filled with another color or other colors to display the photoacoustic-image operation icon Gpa, the Doppler-image operation icon Gdp, and the B-mode-image operation icon Gb on the operation icon display unit 14c in a direction from the close side to the far side in such a manner that the photoacoustic-image operation icon Gpa, the Doppler-image operation icon Gdp, and the B-mode-image operation icon Gb appear to be on top of one another in this order in the direction from the close side to the far side.

In this embodiment, it is preferable that the display order of the operation icons to be displayed on top of one another and the display order of the photoacoustic image Ipa, the Doppler image Idp, and the B-mode image Ib in the superimposed image be associated with each other. For example, when the photoacoustic-image operation icon Gpa, the Doppler-image operation icon Gdp, and the B-mode-image operation icon Gb are overlaid on one another in this order from the close side, it is preferable that the photoacoustic image Ipa, the Doppler image Idp, and the B-mode image Ib also be overlaid on one another in this order in the superimposed image. This allows the device user to intuitively identify associations between the images Ipa, Idp, and Ib and the operation icons Gpa, Gdp, and Gb.

In this example, the display color of each operation icon is preferably the same as the display color of the corresponding image. For example, it is considered that the photoacoustic image Ipa is displayed in, for example, red, the Doppler image Idp is displayed in, for example, yellow, and the B-mode image Ib is displayed in, for example, gray. In this case, it is preferable that the photoacoustic-image operation icon Gpa be displayed in red, the Doppler-image operation icon Gdp be displayed in yellow, and the B-mode-image operation icon Gb be displayed in gray accordingly. Each operation icon is preferably displayed with an indication of the type of the corresponding image. For example, it is preferable that the photoacoustic-image operation icon Gpa be displayed with "PA", which indicates a photoacoustic image, the Doppler-image operation icon Gdp be displayed with "DP", which indicates a Doppler image, and the B-mode-image operation icon Gb be displayed with "B", which indicates a B-mode image. Also in these respects, the device user is able to intuitively identify associations between the images Ipa, Idp, and Ib and the operation icons Gpa, Gdp, and Gb.

As described above, it is not always necessary to associate the display color of an operation icon with the display color of a display image.

Figure 16:
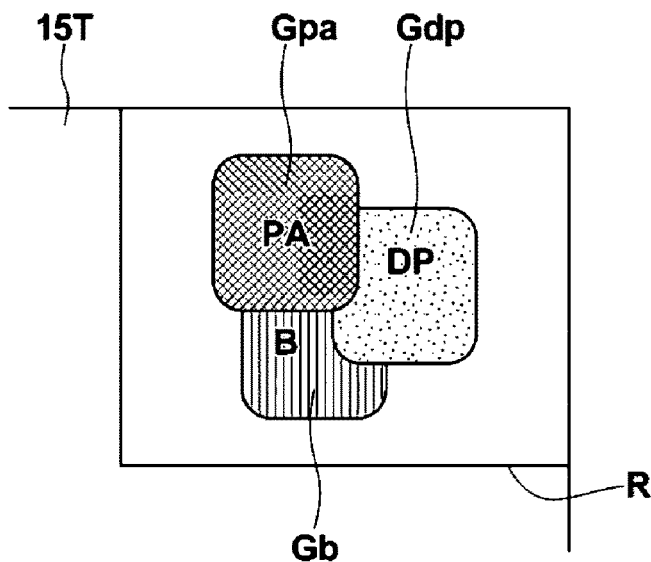
FIG. 16 is a schematic diagram illustrating another state of the operation icons in FIG. 15.

Here, any one of the operation icons Gpa, Gdp, and Gb, for example, the photoacoustic-image operation icon Gpa, is "pressed and held", which is a predetermined operation, thereby changing the display color of the photoacoustic-image operation icon Gpa, which is displayed in red, to any other predetermined color, for example, green. FIG. 16 schematically illustrates a state in which the display color of the photoacoustic-image operation icon Gpa has been changed in this way. Note that when the photoacoustic-image operation icon Gpa whose color has been changed to green is pressed and held again, the display color of the icon Gpa is returned to the original, red.

When the display color of an operation icon is changed, the display color of the acoustic wave image corresponding to the operation icon is preferably also changed. For example, the display color of the photoacoustic-image operation icon Gpa is changed to green, it is preferable that the display color of the photoacoustic image Ipa on the image display unit 14a also be changed to green. It is also preferable that the photoacoustic-image menu icons Fpa on the menu icon display unit 14b (see FIG. 7 and FIG. 10) also be changed to green. The same applies to a case where the Doppler-image operation icon Gdp or the B-mode-image operation icon Gb, other than the photoacoustic-image operation icon Gpa, is pressed and held.

In this embodiment, the display control unit 28 (see FIG. 1) performs control to change the display color of an image and change the display color of an operation icon on the basis of a signal output from the touch panel 15T also acting as an input unit. The display control unit 28 functions as an operation icon display control unit and also functions as an image display control unit.

The display control unit 28 also functions in the way described above when the stacking order of the photoacoustic image Ipa, the Doppler image Idp, and the B-mode image Ib is changed and when the stacking order of the photoacoustic-image operation icon Gpa, the Doppler-image operation icon Gdp, and the B-mode-image operation icon Gb is changed, as described below, as well as when a plurality of kinds of images are displayable as the Doppler image Idp and an image to be displayed is selected.

As previously described, in this embodiment, a color Doppler image and a color flow map in which the spatial distributions of average velocity, variance, power, and/or the like of blood flow are separated by color can be created as Doppler images Idp. The display control unit 28 illustrated in FIG. 1 controls image display such that the color Doppler image or an image indicating the color flow map (hereinafter referred to as a color flow map display image) can be selectively displayed on the image display unit 14a.

The Doppler-image operation icon Gdp is also available for the selective display of the color Doppler image or the color flow map display image described above. That is, each time a "press-and-hold" operation is performed on the Doppler-image operation icon Gdp once as one of the predetermined operations to be performed on the Doppler-image operation icon Gdp, the display of the color Doppler image and the display of the color flow map display image are switched. Such control of a display image is also performed by the display control unit 28 in FIG. 1.

When the color flow map display image is to be displayed, the color flow map display image may be separated by color and displayed in a plurality of colors. In this case, the Doppler-image operation icon Gdp may be displayed in a plurality of colors so as to correspond to the color flow map display image. When the color Doppler image, rather than the color flow map display image, is to be displayed, the Doppler-image operation icon Gdp may be displayed in a single color.

Alternatively, a color Doppler image or a power Doppler image may be selectively displayed as the Doppler image Idp. Also when both images are selectively displayed, for example, each time "press-and-hold" is performed on the Doppler-image operation icon Gdp once, the display control unit 28 illustrated in FIG. 1 switches between the display images.

When a color Doppler image is to be displayed, the color Doppler image may be displayed by color gradation using colors from blue to red, for example. In this case, it is desirable that the Doppler-image operation icon Gdp be displayed by color gradation using colors corresponding to the display color of the color Doppler image. When a power Doppler image is to be displayed, the power Doppler image may be displayed by color gradation using colors from warm color to cold color, for example. In this case, it is desirable that the Doppler-image operation icon Gdp be displayed by color gradation using colors corresponding to the display color of the power Doppler image. FIG. 19 schematically illustrates a state in which the Doppler-image operation icon Gdp is displayed by color gradation.

When a color Doppler image and a power Doppler image are to be selectively displayed, it is preferable that the Doppler-image operation icon Gdp be displayed with characters corresponding to the type of a Doppler image to be displayed. For example, when a color Doppler image is to be displayed, for example, the Doppler-image operation icon Gdp is preferably displayed with the characters "CD". When a power Doppler image is to be displayed, for example, the Doppler-image operation icon Gdp is preferably displayed with the characters "PWD". This facilitates easy understanding of whether an image displayed as a color Doppler image is a color Doppler image or a power Doppler image on the basis of the Doppler-image operation icon Gdp.

When the Doppler-image operation icon Gdp is to be displayed by color gradation, as illustrated in FIG. 19, the gradation bar VB may be displayed and a desired position on the gradation bar VB may be touched to set the degree of gradation of the Doppler-image operation icon Gdp to a preferable state.

Here, a "drag-and-drop" operation can be performed on the operation icons Gpa, Gdp, and Gb on the touch panel 15T with a finger of the user or the like. The drag-and-drop operation may be performed using, for example, input means such as a mouse when, in particular, the operation icon display unit 14c other than the touch panel 15T is applied, for example.

Figure 15:
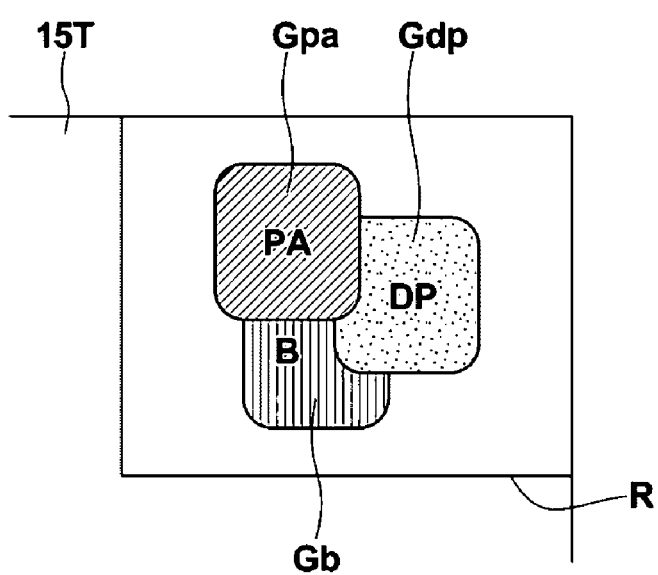
FIG. 15 is a schematic diagram illustrating an example of operation icons.
Figure 17:
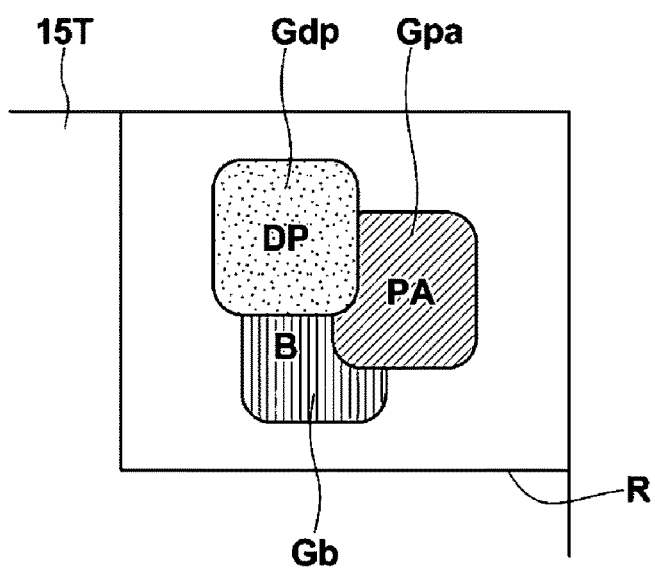
FIG. 17 is a schematic diagram illustrating still another state of the operation icons in FIG. 15.

For example, when the photoacoustic-image operation icon Gpa in the state illustrated in FIG. 15 is dragged and dropped onto the Doppler-image operation icon Gdp, the display of the touch panel 15T is changed in a manner illustrated in FIG. 17. That is, the photoacoustic-image operation icon Gpa, which is displayed closest to the image observer side, is moved to the position one farther from the image observer side, and the Doppler-image operation icon Gdp, which is displayed at the position second closest to the image observer side, is moved to the position closest to the image observer side.

In accordance with the change in the display order of the icons, the display order in the superimposed image displayed on the image display unit 14a is changed. Specifically, the photoacoustic image Ipa, which is displayed closest to the image observer side, is moved to the position second closest to the image observer side, and the Doppler image Idp, which is displayed at the position second closest to the image observer side, is displayed closest to the image observer side. The stacking positions of the operation icons are changed by changing the display positions thereof on the operation icon display unit 14c (see FIG. 1) and by changing how a portion of each operation icon is filled with another color or other colors.

Also in the configuration described above, an advantage that the device user is able to intuitively identify associations between the images Ipa, Idp, and Ib and the operation icons Gpa, Gdp, and Gb, is still maintained.

Figure 18:
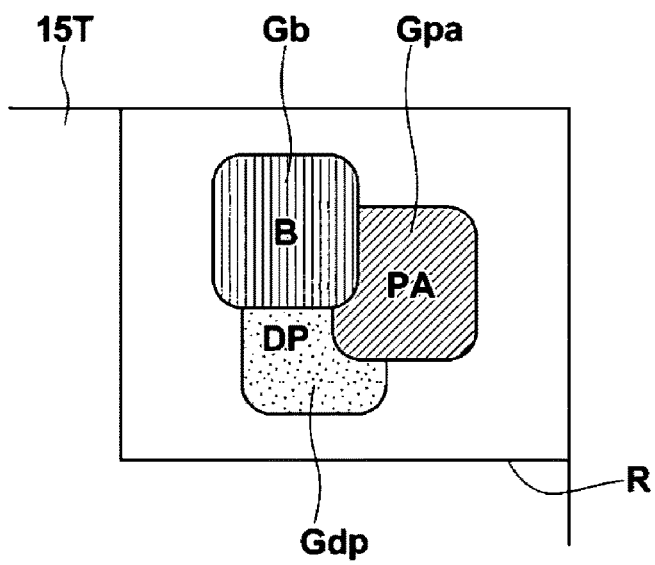
FIG. 18 is a schematic diagram illustrating still another state of the operation icons in FIG. 15.

Furthermore, after the state in FIG. 17 is obtained, when the Doppler-image operation icon Gdp is further dragged and dropped onto the B-mode-image operation icon Gb, the display of the touch panel 15T is changed in a manner illustrated in FIG. 18. That is, the Doppler-image operation icon Gdp, which is displayed closest to the image observer side, is moved to the position two farther from the image observer side (the position farthest from the image observer side), and the B-mode-image operation icon Gb, which is displayed farthest from the image observer side, is moved to the position closest to the image observer side. Accordingly, the display order in the superimposed image is also changed such that the Doppler image Idp is displayed at the position third closest to the image observer side and the B-mode image Ib is displayed closest to the image observer side.

When the stacking order of the display images Ipa, Idp, and Ib and the stacking order of the operation icons Gpa, Gdp, and Gb are changed in the way described above, it is desirable that the positions of the photoacoustic-image menu icons Fpa, the Doppler-image menu icons Fdp, and the B-mode-image menu icons Fb illustrated in FIG. 7 to FIG. 9 in the upward-downward direction (more specifically, the positions thereof in the upward-downward direction on the touch panel 15T) also be changed accordingly so that the correspondence with the stacking order of the images Ipa, Idp, and Ib can be maintained. The same applies to the positions of the menu sheet selection tabs Tpa, Tdp and Tb illustrated in FIG. 10 to FIG. 14 in the left-right direction (more specifically, the positions thereof in the left-right direction on the touch panel 15T).

Figure 20:
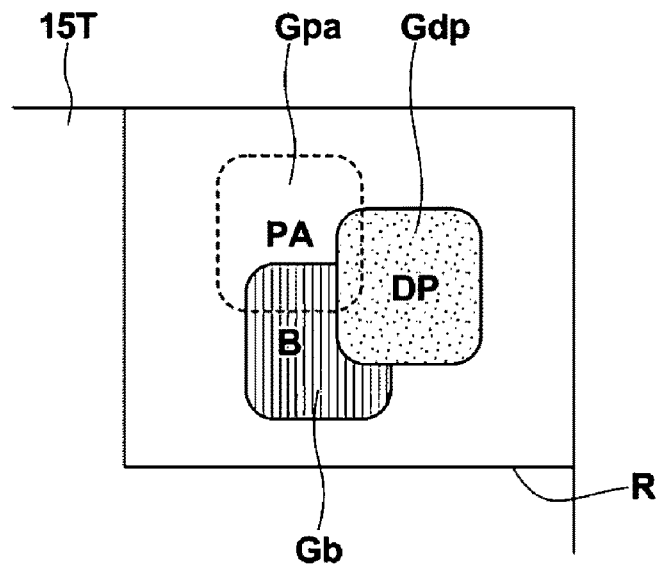
FIG. 20 is a schematic diagram illustrating still another state of the operation icons in FIG. 15.

In this embodiment, furthermore, the display or hiding of the photoacoustic image Ipa, the Doppler image Idp, and the B-mode image Ib, which is one of the predetermined display states, can be controlled. The following describes this point. As illustrated in FIG. 20, for example, when a "single touch and tap" operation is performed on one of the photoacoustic-image operation icon Gpa, the Doppler-image operation icon Gdp, and the B-mode-image operation icon Gb as one of the predetermined operations to be applied, the operation icon to which this operation is applied is brought into non-display (a hidden state).

FIG. 20 illustrates, as an example, a state in which the photoacoustic-image operation icon Gpa is in a non-display state. In addition to this, the photoacoustic image Ipa, which is a display image selected using the photoacoustic-image operation icon Gpa, is also brought into a non-display state. Note that when the "single touch and tap" operation described above is performed on a portion of the touch panel 15T where the photoacoustic-image operation icon Gpa would have been displayed, the photoacoustic-image operation icon Gpa and the photoacoustic image Ipa are returned to a displayed state.

The display or non-display control of the photoacoustic-image operation icon Gpa and the photoacoustic image Ipa described above is also performed by the display control unit 28 illustrated in FIG. 1.

Figure 21:
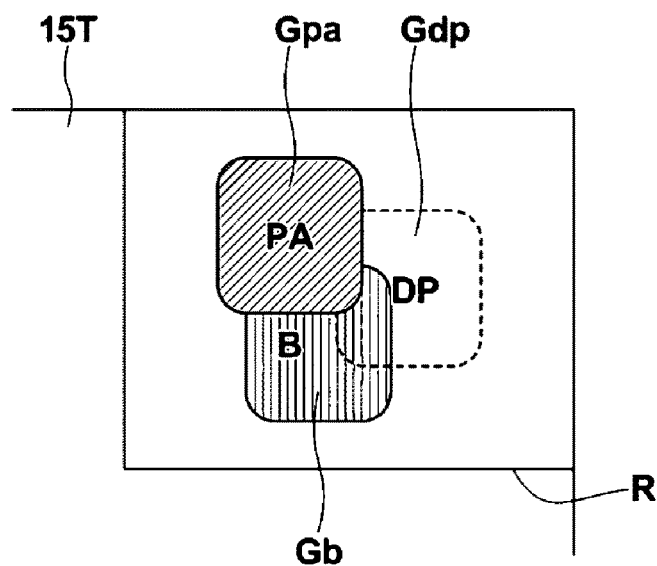
FIG. 21 is a schematic diagram illustrating still another state of the operation icons in FIG. 15.

Also when any operation icon other than the photoacoustic-image operation icon Gpa is operated, similar display state control is performed. For example, FIG. 21 illustrates an example in which the Doppler-image operation icon Gdp is in a non-display state. In this case, the Doppler image Idp, which is a display image selected using the Doppler-image operation icon Gdp, is also brought into a non-display state.

The configuration described above achieves an advantage in that an image that remains in a display state can be well observed without being occluded by an image brought into a non-display state.

Now, a more detailed icon display style in which one or more of the photoacoustic-image operation icon Gpa, the Doppler-image operation icon Gdp, and the B-mode-image operation icon Gb are in a non-display state and the other operation icon(s) is in a display state in the way described above will be described, taking the case in FIG. 20 as an example.

In this case, the Doppler-image operation icon Gdp, which is in the displayed state, is basically displayed in a first form including the same display color as that of the Doppler image Idp selected using the icon Gdp. Further, the B-mode-image operation icon Gb, which is in the displayed state, is also basically displayed in the first form including the same display color as that of the B-mode image Ib selected using the icon Gb.

In contrast, the photoacoustic-image operation icon Gpa, which is in the hidden state, is displayed in a second form different from the first form.

As an example, the first form is regarded as a form in which the Doppler-image operation icon Gdp is displayed in a display color identical to that of the Doppler image Idp and the B-mode-image operation icon Gb is displayed in a display color identical to that of the B-mode image Ib. In contrast, the photoacoustic-image operation icon Gpa to be displayed in the second form is displayed in a form in which, as illustrated in FIG. 20, the icon is represented by a contour. The contour may be indicated by a broken line. Alternatively, the display of such a contour may be omitted.

As another example, the first form is regarded as a form in which the Doppler-image operation icon Gdp is displayed in a display color identical to that of the Doppler image Idp and the B-mode-image operation icon Gb is displayed in a display color identical to that of the B-mode image Ib. In contrast, the photoacoustic-image operation icon Gpa displayed in the second form described above is displayed in achromatic gray.

As still another example, the first form is regarded as a form in which the Doppler-image operation icon Gdp and the B-mode-image operation icon Gb are displayed such that a colored portion displayed in the display color of each of the Doppler image Idp and the B-mode image Ib contains a character in a color different from the color of the colored portion. The character is typically a character indicating an image selected using the corresponding operation icon. In contrast, the photoacoustic-image operation icon Gpa displayed in the second form described above is displayed with the inverted colors of the colored portion and the character in the first form.

As still another example, the first form is regarded as a form in which the Doppler-image operation icon Gdp is displayed in a display color identical to that of the Doppler image Idp and the B-mode-image operation icon Gb is displayed in a display color identical to that of the B-mode image Ib. In contrast, the photoacoustic-image operation icon Gpa displayed in the second form described above is displayed in such a manner that a predetermined sign, for example, a predetermined mark and/or oblique lines, is applied to the icon.

In each of the four examples described above, the photoacoustic-image operation icon Gpa displayed in the second form described above may be displayed with a character whose font is italic or the like or whose size is halved or the like, compared with that in the normal display case. This clarifies that the acoustic wave image selected using the corresponding operation icon is in a non-display state.

As illustrated in FIG. 20, the photoacoustic-image operation icon Gpa represented by a contour is displayed such that the interior of the contour is basically transparent. In addition to this, the photoacoustic image Ipa selected using the photoacoustic-image operation icon Gpa is also transparent, that is, is in a non-display state.

In this case, for example, when a double-click operation is performed at a point on the touch panel 15T, it is desirable that the gradation bar VB illustrated in FIG. 19 be displayed at any position on the touch panel 15T and that any position on the gradation bar VB be touched or clicked to make the display of the photoacoustic-image operation icon Gpa and the photoacoustic image Ipa in a transparent manner adjustable.

Figure 22:
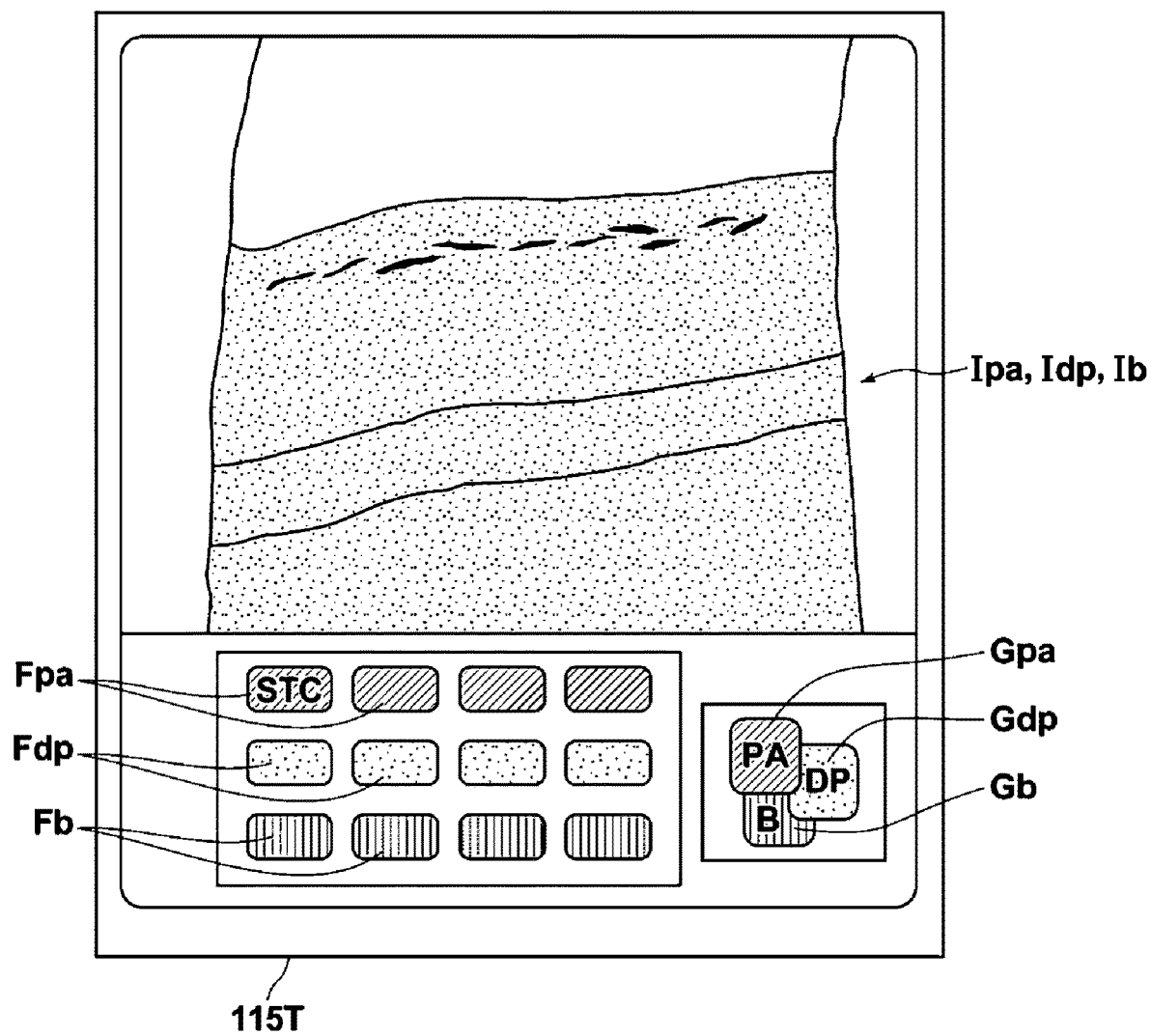
FIG. 22 is a schematic diagram illustrating an example of a device that displays acoustic wave images and icons.

As an embodiment different from the embodiment described above, as illustrated in FIG. 22, the photoacoustic image Ipa, the Doppler image Idp, the B-mode image Ib, the photoacoustic-image menu icons Fpa, the Doppler-image menu icons Fdp, the B-mode-image menu icons Fb, the photoacoustic-image operation icon Gpa, the Doppler-image operation icon Gdp, and the B-mode-image operation icon Gb may be all displayed on one image display unit such as a touch panel 115T.

Figure 23:
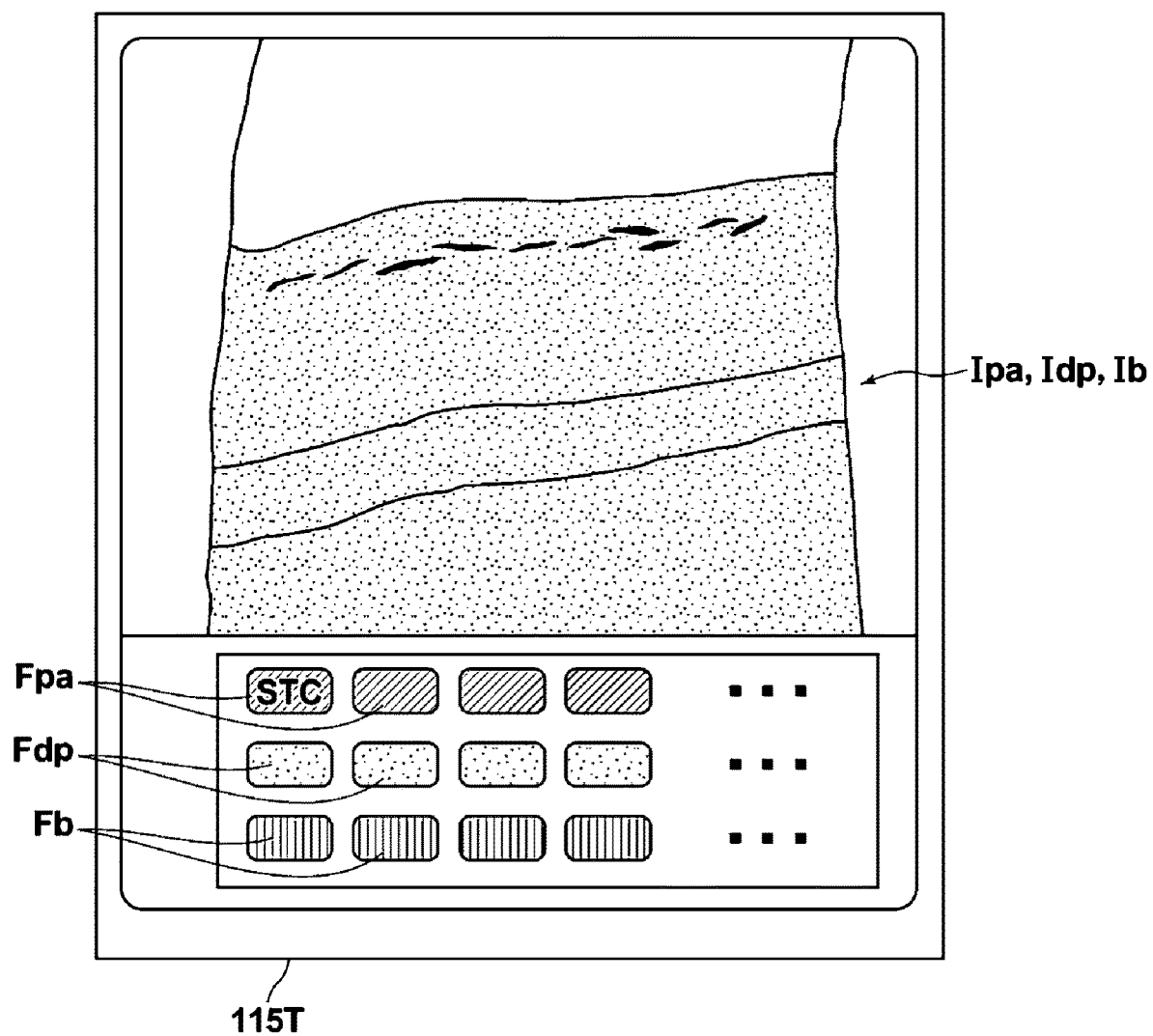
FIG. 23 is a schematic diagram illustrating still another example of the device that displays acoustic wave images and icons.

Alternatively, as illustrated in FIG. 23, the photoacoustic image Ipa, the Doppler image Idp, the B-mode image Ib, the photoacoustic-image menu icons Fpa, the Doppler-image menu icons Fdp, and the B-mode-image menu icons Fb may be displayed on one image display unit such as a touch panel 115T, and the photoacoustic-image operation icon Gpa, the Doppler-image operation icon Gdp, and the B-mode-image operation icon Gb may be displayed on any other image display unit.

Figure 24:
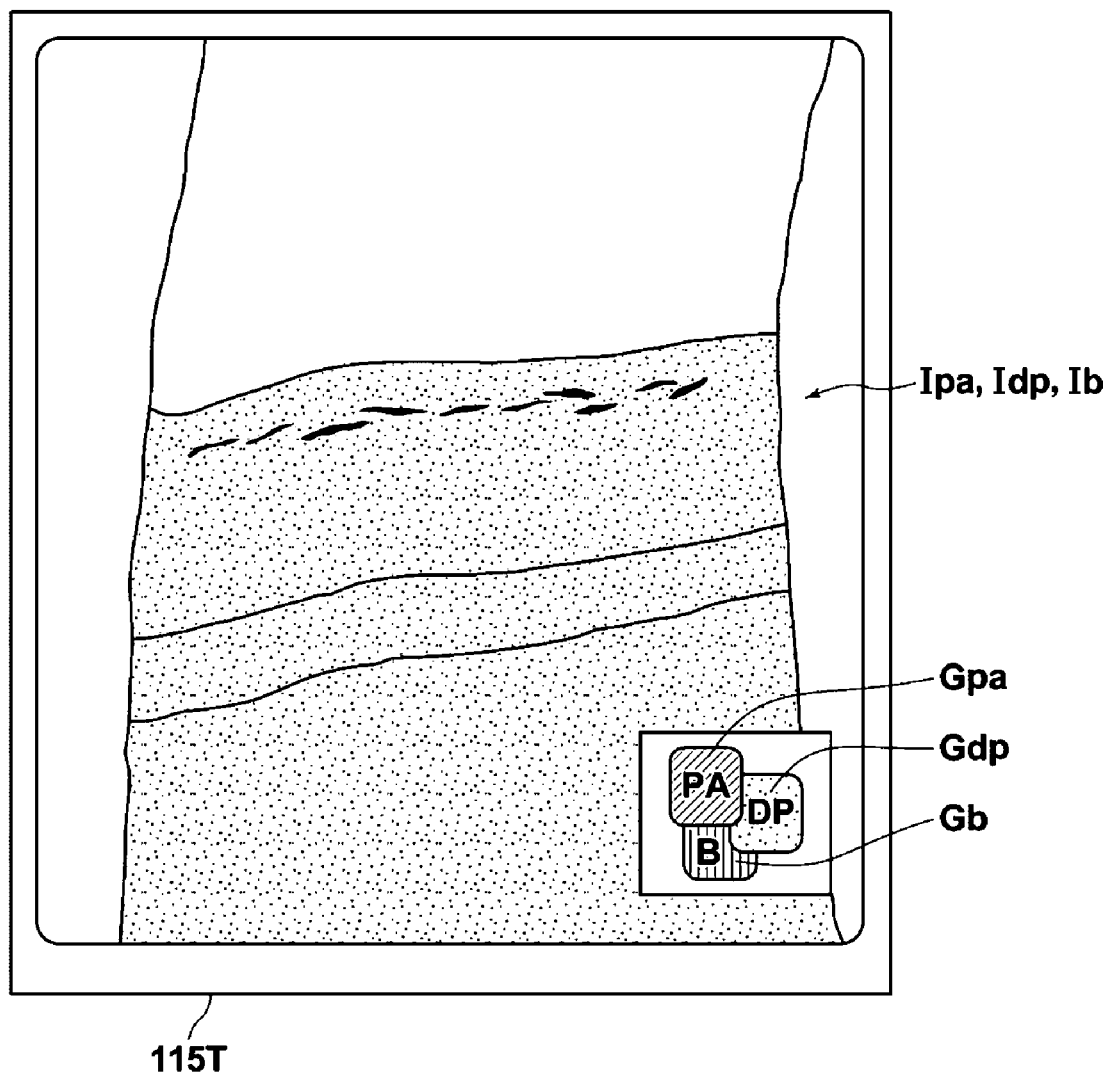
FIG. 24 is a schematic diagram illustrating still another example of the device that displays acoustic wave images and icons.

Furthermore, as illustrated in FIG. 24, the photoacoustic image Ipa, the Doppler image Idp, the B-mode image Ib, the photoacoustic-image operation icon Gpa, the Doppler-image operation icon Gdp, and the B-mode-image operation icon Gb may be displayed one image display unit such as a touch panel 115T, and the photoacoustic-image menu icons Fpa, the Doppler-image menu icons Fdp, and the B-mode-image menu icons Fb may be displayed on any other image display unit.

An issue has been previously described in which when the stacking order of the photoacoustic image Ipa, the Doppler image Idp, and the B-mode image Ib is changed, an image on the close side may hide image(s) therebehind or the image(s) may be difficult to view depending on the colors of the images. This issue may also, of course, arise when the display positions (stacking positions) of the display images are changed by operating the operation icons Gpa, Gdp, and Gb. To address this issue, it is conceivable to display a plurality of images not in their unique display colors but in display colors corresponding to the display order of the images. For example, in the display of four images, the first, second, third, and fourth images in the direction from the close side to the far side are assumed to be displayed in gray, yellow, orange, and red, respectively. In this case, focusing on one of the images, the display color is changed in accordance with a change in display order.

The configuration described above prevents a red image from being displayed on the close side and a gray image from being displayed on the far side if the display order of a plurality of images is changed, which does not lead to the issue described above. Examples of the correspondence between the display order and the display colors of the images include, in addition to the correspondence described above, a relationship between images whose colors are changed from low saturation to high saturation in the direction from the close side to the far side, and a relationship between images whose colors are changed from cold colors to warm colors in the direction from the close side to the far side. The foregoing method can also be applied not only to when the display positions of the display images are changed by operating the operation icons Gpa, Gdp, and Gb but also when the display positions of the images are changed by operating the selection tabs Tpa, Tdp, and Tb illustrated in FIG. 10.

The foregoing has described an embodiment in which the B-mode image Ib is further displayed in addition to the photoacoustic image Ipa as a first acoustic wave image in the present invention and the Doppler image Idp as a second acoustic wave image in the present invention. If the B-mode image Ib is considered to be a second acoustic wave image in the present invention, advantages achieved by the present invention can also be obtained in this case. In actuality, the photoacoustic image Ipa may be displayed as a first acoustic wave image in the present invention, and only the B-mode image Ib may be displayed as a second acoustic wave image in the present invention. Also in this case, advantages achieved by the present invention can be obtained.

Furthermore, also when three or more acoustic wave images based on signals obtained by detecting reflected acoustic waves, which are acoustic waves emitted to the subject M and reflected within the subject M, are to be displayed in addition to a first acoustic wave image based on signals obtained by detecting photoacoustic waves generated from within the subject M which has received light L emitted to the subject M, advantages achieved by the present invention can be obtained if one of the three images is considered to be a second acoustic wave image in the present invention.

From the foregoing, it is apparent that the present invention can also be applied to a case where two or more acoustic wave images based on signals obtained by detecting the reflected acoustic waves described above are to be displayed.

What is claimed is:

1. An acoustic wave image display device in a system for displaying a first acoustic wave image and a second acoustic wave image on image display unit, the first acoustic wave image being generated on the basis of detected signals of photoacoustic waves generated, from within a subject, by the subject receiving light emitted to the subject, the second acoustic wave image being generated on the basis of detected signals of reflected acoustic waves, which are acoustic waves transmitted to the subject and reflected within the subject, the acoustic wave image display device comprising:

an image display control unit that causes the first acoustic wave image and the second acoustic wave image to be displayed on top of each other on the image display unit in different display colors;

operation icon display unit for displaying a first operation icon for selecting the first acoustic wave image and a second operation icon for selecting the second acoustic wave image; and an operation icon display control unit that causes the first operation icon and the second operation icon to be displayed on top of each other on the operation icon display unit in a display order identical to a display order of the first acoustic wave image and the second acoustic wave image that are displayed on top of each other on the image display unit, wherein the display order of the first operation icon and the second operation icon remain the same regardless of whether the first operation icon and the second operation icon are selected, and wherein the display order of the first operation icon and the second operation icon are identical to the display order of the first acoustic wave image and the second acoustic wave image regardless of whether the first operation icon and the second operation icon are selected.

2. The acoustic wave image display device according to claim 1, further comprising:

menu icon display unit for displaying a first menu icon group for designating a process to be performed on the first acoustic wave image and a second menu icon group for designating a process to be performed on the second acoustic wave image; and a menu icon display control unit that causes the first menu icon group and the second menu icon group to be displayed on the menu icon display unit in separate groups.

3. The acoustic wave image display device according to claim 2, wherein the menu icon display unit has a different display screen from the image display unit.

4. The acoustic wave image display device according to claim 2, wherein the menu icon display unit has a display screen common to the image display unit.

5. The acoustic wave image display device according to claim 1, wherein the image display control unit changes the display order of the first acoustic wave image and the second acoustic wave image on the image display unit in accordance with an operation of changing an order in which the first operation icon and the second operation icon are stacked on top of each other.

6. The acoustic wave image display device according to claim 5, wherein the image display control unit causes the first acoustic wave image and the second acoustic wave image to be displayed in display colors determined in advance in accordance with a display order on the image display unit.

7. The acoustic wave image display device according to claim 6, wherein the image display control unit causes, among the first acoustic wave image and the second acoustic wave image, an acoustic wave image located on a close side in the display order to be displayed in a display color that makes a display color of an acoustic wave image located on a far side in the display order visible.

8. The acoustic wave image display device according to claim 1, wherein each time a predetermined operation is applied to the first operation icon once, the image display control unit switches a display state between a state in which the first acoustic wave image is displayed on the image display unit and a state in which the first acoustic wave image is hidden on the image display unit, and each time a predetermined operation is applied to the second operation icon once, the image display control unit switches a display state between a state in which the second acoustic wave image is displayed on the image display unit and a state in which the second acoustic wave image is hidden on the image display unit.

9. The acoustic wave image display device according to claim 8, wherein the operation icon display control unit causes the operation icon for selecting, from among the first acoustic wave image and the second acoustic wave image, an acoustic wave image brought into the state in which the acoustic wave image is displayed to be displayed in a first form, and causes the operation icon for selecting, from among the first acoustic wave image and the second acoustic wave image, an acoustic wave image brought into the state in which the acoustic wave image is hidden to be displayed in a second form different from the first form.

10. The acoustic wave image display device according to claim 9, wherein the first form is a form in which the operation icon is displayed in color, and the second form is a form in which the operation icon is represented by a contour.

11. The acoustic wave image display device according to claim 9, wherein the first form is a form in which the operation icon is displayed in color, and the second form is a form in which the operation icon is displayed in an achromatic color.

12. The acoustic wave image display device according to claim 9, wherein the first form is a form in which a colored portion contains a character in a color different from a color of the colored portion to show an operation icon, and the second form is a form in which the color of the colored portion and the color of the character in the first form are inverted.

13. The acoustic wave image display device according to claim 9, wherein the first form is a form in which the operation icon is displayed in color, and the second form is a form in which a predetermined sign is applied to the operation icon.

14. The acoustic wave image display device according to claim 1, wherein the operation icon display control unit causes, among the first operation icon and the second operation icon, an operation icon located on a close side of the operation icon display unit in the display order to be displayed in a transparent manner to make an operation icon located on a far side of the operation icon display unit in the display order visible, and wherein the image display control unit causes, among the first acoustic wave image and the second acoustic wave image, an acoustic wave image located on the close side in the display order to be displayed in a transparent manner to make an acoustic wave image located on the far side in the display order visible.

15. The acoustic wave image display device according to claim 14, wherein at least one of the operation icon display control unit or the image display control unit is capable of adjusting a degree of transparency in the display in a transparent manner.

16. The acoustic wave image display device according to claim 1, wherein the operation icon display unit has a different display screen from the image display unit.

17. The acoustic wave image display device according to claim 1, wherein the operation icon display unit has a display screen common to the image display unit.

18. An acoustic wave image display method for displaying a first acoustic wave image and a second acoustic wave image in color on image display unit, the first acoustic wave image being generated on the basis of detected signals of photoacoustic waves generated, from within a subject, by the subject receiving light emitted to the subject, the second acoustic wave image being generated on the basis of detected signals of reflected acoustic waves, which are acoustic waves transmitted to the subject and reflected within the subject, the acoustic wave image display method comprising:

displaying the first acoustic wave image and the second acoustic wave image on top of each other in different display colors;

displaying, on operation icon display unit, a first operation icon for selecting the first acoustic wave image and a second operation icon for selecting the second acoustic wave image; and displaying the first operation icon and the second operation icon on top of each other in a display order identical to a display order of the first acoustic wave image and the second acoustic wave image that are displayed on top of each other on the image display unit, wherein the display order of the first operation icon and the second operation icon remain the same regardless of whether the first operation icon and the second operation icon are selected, and wherein the display order of the first operation icon and the second operation icon are identical to the display order of the first acoustic wave image and the second acoustic wave image regardless of whether the first operation icon and the second operation icon are selected.

* * * * *